US011840710B2

(12) United States Patent
Sheldon et al.

(10) Patent No.: US 11,840,710 B2
(45) Date of Patent: Dec. 12, 2023

(54) METHODS FOR PURIFICATION OF RECOMBINANT AAV VECTORS

(71) Applicant: Genzyme Corporation, Cambridge, MA (US)

(72) Inventors: Paulene McLean Quigley Sheldon, Seattle, WA (US); Peter S. Gagnon, San Clemente, CA (US); Gina Nichols, Everett, WA (US); Barbara A. Thorne, Sammamish, WA (US)

(73) Assignee: Genzyme Corporation, Cambridge, MA (US)

( * ) Notice: Subject to any disclaimer, the term of this patent is extended or adjusted under 35 U.S.C. 154(b) by 0 days.

(21) Appl. No.: 17/035,480

(22) Filed: Sep. 28, 2020

(65) Prior Publication Data

US 2021/0139860 A1 May 13, 2021

Related U.S. Application Data

(63) Continuation of application No. 16/878,375, filed on May 19, 2020, now abandoned, which is a continuation of application No. 16/006,210, filed on Jun. 12, 2018, now Pat. No. 10,696,952, which is a continuation of application No. 13/328,306, filed on Dec. 16, 2011, now Pat. No. 10,017,746, which is a continuation of application No. PCT/US2010/038897, filed on Jun. 16, 2010.

(60) Provisional application No. 61/187,601, filed on Jun. 16, 2009.

(51) Int. Cl.

| | |
|---|---|
| ***C12N 7/00*** | (2006.01) |
| ***C07K 14/005*** | (2006.01) |
| ***C12N 15/86*** | (2006.01) |

(52) U.S. Cl.
CPC .............. *C12N 7/00* (2013.01); *C07K 14/005* (2013.01); *C12N 15/86* (2013.01); *C12N 2750/14151* (2013.01)

(58) Field of Classification Search
None
See application file for complete search history.

(56) References Cited

U.S. PATENT DOCUMENTS

| | | | |
|---|---|---|---|
| 6,566,118 | B1 | 5/2003 | Atkinson |
| 6,723,551 | B2 | 4/2004 | Kotin |
| 6,989,264 | B2 | 1/2006 | Atkinson |
| 6,995,006 | B2 | 2/2006 | Atkinson |
| 7,015,026 | B2 | 3/2006 | Oriordan |
| 2004/0110266 | A1 | 6/2004 | Chiorini |
| 2011/0311724 | A1 | 12/2011 | Jensen |

FOREIGN PATENT DOCUMENTS

| | | | |
|---|---|---|---|
| JP | H11511326 | A | 10/1999 |
| JP | 2012516278 | A | 7/2012 |
| WO | 1999011764 | A2 | 3/1999 |
| WO | 2006074664 | A1 | 7/2006 |
| WO | 2008113011 | A2 | 9/2008 |
| WO | 2010148143 | A1 | 12/2010 |

OTHER PUBLICATIONS

Sauerbrei and Wutzler, Testing Thermal Resistance of Viruses, 2009, Archives of Virology, vol. 154, pp. 115-119.*
Ali, R.R. et al. (May 1, 1996). "Gene Transfer Into The Mouse Retina Mediated By An Adeno-Associated Viral Vector," Human Molecular Genetics 5(5):591-594.
Arakawa, T. et al. (2008). "Solvent Modulation of Chromatography," Journal of Japanese Biochemistry (Seikagaku) 80:45-51. (Partial English Translation).
Arakawa, T. et al. (Jul. 1, 2008). "Solvent Modulation of col. Chromatography," Protein & Peptide Letters 15(6):544-555.
Azevedo, M. et al. (Dec. 12, 2008), "Integrated Process for the Purification of Antibodies Combining Aqueous Two-Phase Extraction, Hydrophobic Interaction Chromatography and size-exclusion Chromatography", Journal of Chromatography-A, 1213(2):154-161.
Berns, K. (1990) "Parvoviridae and Their Replication," Chapter 62 in Virology, Second Edition, Raven Press, Ltd., New York, pp. 1743-1764.
Brument, N. et al. (Nov. 2002) "A Versatile and Scalable Two-Step Ion-Exchange Chromatography Process for the Purification of Recombinant Adeno-Associated Virus Serotypes-2 and -5," Mol. Therapy 6(5):678-686.
Burova, E. et al. (Oct. 2005). "Chromatographic Purification of Recombinant Adenoviral and Adeno-Associated Viral Vectors: Methods and Implications," Gene Ther. 12(1):S5-S17.
Carter, B.J. et al. (1990). "AAV DNA Replication, Integration, and Genetics," Chapter 11 in Handbook of Parvoviruses, vol. I, CRC Press, pp. 169-228.
Chahal, P.S. et al. (Jan. 2007). "Primary Recovery and Chromatographic Purification of Adeno-Associated Virus Type 2 Produced By Baculovirus/Insect Cell System," J Viral. Methods 139(1):61-70.
Chirico, J. et al. (1998) "Optimization of Packaging of Adeo-Associated Virus Gene Therapy Vectors Using Plasmid Transfections," J Viral. Methods 76:31-41.
Clark, K.R. et al. (Apr. 10, 1999). "Highly Purified Recombinant Adeno-Associated Virus Vectors are Biologically Active and Free of Detectable Helper and Wild-Type Viruses," Hum. Gene Ther. 10(6):1031-1039.
Gagnon, G. et al. (Mar. 4-6, 2009). "Multimodal Interactions of IgG, Fab, F(ab')2, Fc, and Aggregates with Hydroxyapatite," 22nd International IBC Conference on Antibody Production and Development, Mar. 4-6, 2009, Carlsbad, California, USA; 1 page.

(Continued)

*Primary Examiner* — Benjamin P Blumel
(74) *Attorney, Agent, or Firm* — Morrison & Foerster LLP

(57) ABSTRACT

Provided herein are methods for the purification of recombinant adeno-associated virus (rAAV) vectors that can be used for gene transfer and specifically for gene therapy or vaccination. Recombinant AAV vectors of the invention are substantially free of in-process impurities, including production components such as cellular nucleic acids, cellular proteins, helper virus, and media components.

24 Claims, 7 Drawing Sheets

(56) References Cited

OTHER PUBLICATIONS

Gagnon, P. et al. (1996). "Method for Obtaining Unique Selectivities in Ion-Exchange Chromatography by Addition of Organic Polymers to the Mobile Phase," J. Chromatog. 743(1):51-55.
Gagnon, P. et al. (Feb. 2006). "A Ceramic Hydroxyapatite-Based Purification Platform," BioProcess Int'l 4:50-60.
Gao, G. et al. (Oct. 10, 2000). "Purification of Recombinant Adeno-Associated Virus Vectors by Column Chromatography and Its Performance in Vivo," Hum. Gene Therapy 11:2079-2091.
International Search Report dated Aug. 17, 2010, for PCT Patent Application No. PCT/US2010/38897, filed on Jun. 16, 2010, one page.
Kaludov, N. et al. (Jul. 1, 2002) "Scalable Purification of Adeno-Associated Virus Type 2, 4, or 5 Using Ion-Exchange Chromatography," Human Gene Therapy 13:1235-1243.
Kawasaki, T. et al. (1990). "Fundamental Study of Hydroxyapatite High-Performance Liquid Chromatography," J. of Chromatography 515:125-148.
Muzycka, N. (1992). "Use of Adeno-Associated Virus as a General Transduction Vector for Mammalian Cells," Current Topics in Microbiology and Immunology 158:97-129.
O'Riordan, C.R. et al. (2000). "Scaleable Chromatographic Purification Process for Recombinant Adeno-Associated Virus (rAAV)," Journal of Gene Medicine 2:444-454.
Paul, R.W. et al. (1993). "Increased Viral Titer Through Concentration of Viral Harvests from Retroviral Packaging Lines," Human Gene Therapy 4:609-615.
Ruffing, M. et al. (1994). "Mutations in the Carboxy Terminus of Adeno-Associated Virus 2 Capsid Proteins Affect Viral Infectivity:Lack of an RGD Integrin-Binding Motif," J of General Virology 75: 3385-3392.
Smith, R.H. et al. (2008) "Chromatography-Based Purification of Adeno-Associated Virus", Chapter 2 in Methods in Molecular Biology, vol. 2, pp. 37-54.
Srivastava, A. et al. (Feb. 1983) "Nucleotide Sequence and Organization of the Adeno-Associated Virus 2 Genome," J of Virology. 45(2):555-564.
Supplementary European Search Report dated Apr. 29, 2013, for EP Application No. 10790155.5, filed on Jun. 16, 2010, nine pages.
Urabe, M. et al. (Apr. 2006, e-pub. Feb. 13, 2006). "Removal of Empty Capsids from Type 1 Adeno-Associated Virus Vector Stocks by Anion-Exchange Chromatography Potentiates Transgene Expression," Mol. Therapy 13(4):823-828.
Wright, J.F. et al. (Jul. 2005, e-pub Apr. 9, 2005). "Identification of Factors That Contribute to Recombinant AAVF2 Particle Aggregation and Methods to Prevent its Occurrence During Vector Purification and Formulation," Molecular Therapy 12(1):171-178.
Written Opinion dated Aug. 17, 2010, for PCT Patent Application No. PCT/US2010/38897, filed on Jun. 16, 2010, seven pages.
Xiao, X. et al. (Nov. 1996). "Efficient Long-Term Gene Transfer into Muscle Tissue of Immunocompetent Mice by Adeno-Associated Virus Vector," J. Virology 70(11):8098-8108.
Zolotukhin, S. et al. (1999). "Recombinant Adeno-Associated Virus Purification using Novel Methods Improves Infectious Titer and Yield," Gene Therapy 6(6):973-985.
Zolotukhin, S. et al. (2002). "Production and Purification of Serotype 1, 2, and 5 Recombinant Adeno-Associated Viral Vectors," Methods 28(2):158-167.

* cited by examiner

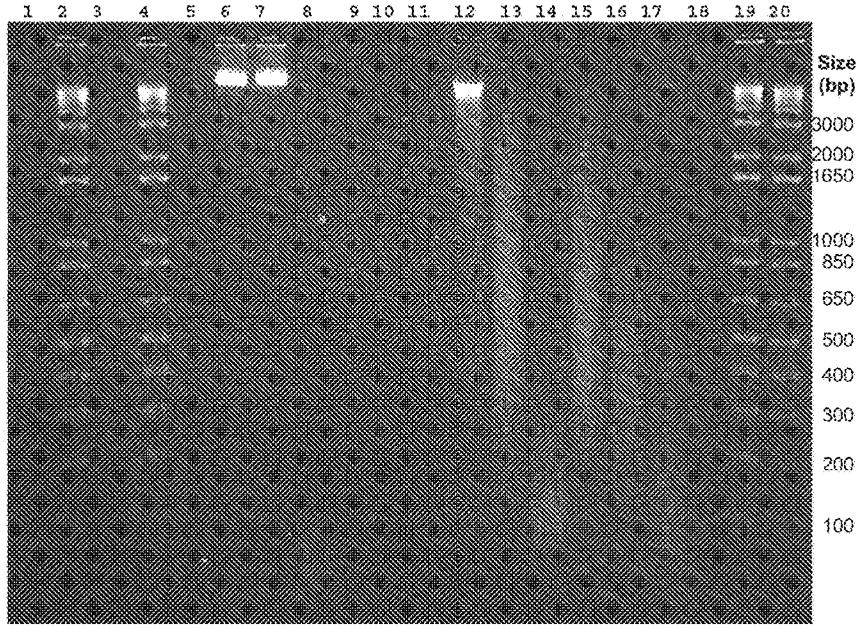

| Lane | Sample |
|---|---|
| 1 | Buffer only |
| 2 | Ladder in TE |
| 3 | - |
| 4 | Ladder in post-clarification feedstream (PCLF) |
| 5 | - |
| | Controls |
| 6 | λ DNA in PCLF (no Benz.) |
| 7 | stop control (λ +PCLF+EDTA+Benz.) |
| 8 | positive control (λ DNA in buffer + Benz.) |
| 9 | PCLF from production lot |
| 10 | Benzonase sample from production lot |
| 11 | AEX FT sample from production lot |
| | Spike digests |
| 12 | 5 min at 15°C |
| 13 | 20 min at 15°C |
| 14 | 62 min at 15°C |
| 15 | 5 min at 37°C |
| 16 | 20 min at 37°C |
| 17 | 62 min at 37°C |
| 18 | - |
| 19 | Ladder in PCLF |
| 20 | Ladder in TE |

FIG. 1

| | Load ratio for 1% breakthrough | % Recovered in Elution |
|---|---|---|
| Serum NO PEG | ~ 2 | NA |
| Serum Free NO PEG | ~ 6 | NA |
| Serum + PEG | >150 | 71% |
| Serum Free + PEG | >150 | 69% |

A

| Fraction | CFT | CHT |
|---|---|---|
| FT | 0% | 0% |
| PO4 | 1% | 2% |
| WII/III | 0% | 0% |
| Elution | **71%** | **65%** |
| Mass Balance | 72% | 68% |

METHODS FOR PURIFICATION OF RECOMBINANT AAV VECTORS

CROSS-REFERENCE TO RELATED APPLICATIONS

This application is a continuation of U.S. patent application Ser. No. 16/878,375, filed May 19, 2020, which is a continuation of U.S. patent application Ser. No. 16/006,210, filed Jun. 12, 2018, now U.S. Pat. No. 10,696,952, which is a continuation of U.S. patent application Ser. No. 13/328,306, filed Dec. 16, 2011, now U.S. Pat. No. 10,017,746, which is a continuation of International Patent Application No. PCT/US2010/038897, filed Jun. 16, 2010, which claims the priority benefit of U.S. provisional application No. 61/187,601, filed Jun. 16, 2009, each of which is incorporated herein by reference in its entirety.

FIELD OF THE INVENTION

The present invention relates generally to the field of purification of recombinant adeno-associated virus (rAAV) vectors that can be used for gene transfer and specifically for gene therapy or vaccination. More specifically, it relates to methods for purification of recombinant rAAV vectors that are substantially free of in-process production components such as cellular nucleic acids, cellular proteins, helper virus, and media components.

BACKGROUND OF THE INVENTION

Adeno-associated viruses (AAV) have unique features that make them attractive as vectors for gene therapy and genetics vaccines. AAV infection of cells in culture is noncytopathic, and natural infection of humans and other animals is silent, asymptomatic, and not implicated in the etiology of any human disease. Moreover, AAV infects a wide range of cell types including many mammalian cells, allowing the possibility of targeting many different tissues in vivo. AAV infects slowly dividing and non-dividing cells and can persist essentially for the lifetime of those cells as a transcriptionally active nuclear episome (extrachromosomal element). Integrated copies of rAAV vector in organs such as liver or muscle are very rare. Efficient long-term gene transfer has been reported in a number of cell types including eye, CNS, and muscle. See, e.g., X. Xiao et al, *J. Virol.* 70(11):8098-8108 (1996); R. R. Ali et al., *Hum. Mol. Genet.* 5(5):591-94 (1996). Current clinical studies have largely focused on the use of serotype 2 rAAV vectors, but a number of reports have demonstrated that other AAV serotypes including rAAV-1, rAAV-4, rAAV-5 and rAAV-8 have unique in vivo bio-distribution which make them attractive viral serotypes to test in clinical trials.

Adeno-associated virus (AAV) is a replication-deficient parvovirus, the single-stranded DNA genome of which is about 4.7 kb in length including 145 nucleotide inverted terminal repeat (ITRs). The nucleotide sequence of the AAV serotype 2 (AAV2) genome is presented in Srivastava et al., *J. Virol.,* 45: 555-564 (1983) as corrected by Ruffing et al., *J. Gen. Virol.,* 75: 3385-3392 (1994). Cis-acting sequences directing viral DNA replication (rep), encapsidation/packaging and host cell chromosome integration are contained within the ITRs. Three AAV promoters, p5, p19, and p40 (named for their relative map locations), drive the expression of the two AAV internal open reading frames encoding rep and cap genes. The two rep promoters (p5 and p19), coupled with the differential splicing of the single AAV intron at nucleotides 2107 and 2227, result in the production of four rep proteins (rep78, rep68, rep52, and rep40) from the rep gene. Rep proteins possess multiple enzymatic properties which are ultimately responsible for replicating the viral genome. The cap gene is expressed from the p40 promoter and it encodes the three capsid proteins VP1, VP2, and VP3. Alternative splicing and non-consensus translational start sites are responsible for the production of the three related capsid proteins. A single consensus polyadenylation site is located at map position 95 of the AAV genome. The life cycle and genetics of AAV are reviewed in Muzyczka, *Current Topics in Microbiology and Immunology,* 158: 97-129 (1992).

AAV particles comprise a proteinaceous capsid having three capsid proteins, VP1, VP2 and VP3, which enclose a ~4.6 kb linear single-stranded DNA genome. Individual particles package only one DNA molecule strand, but this may be either the plus or minus strand. Particles containing either strand are infectious, and replication occurs by conversion of the parental infecting single strand to a duplex form, and subsequent amplification, from which progeny single strands are displaced and packaged into capsids. Duplex or single-strand copies of AAV genomes (sometimes referred to as "proviral DNA" or "provirus") can be inserted into bacterial plasmids or phagemids, and transfected into adenovirus-infected cells. See Carter, Handbook of Parvoviruses, Vol. I, pp. 169-228 (1989), and Berns, Virology, pp. 1743-1764, Raven Press, (1990) for a general review of AAV.

rAAV vector production generally requires four common elements: 1) a permissive host cell for replication; 2) helper virus function which can be supplied by suitable helper viruses such as adenovirus or herpes virus, or alternatively by plasmid constructs containing the minimal adenoviral helper functions; 3) a trans-packaging rep-cap construct; and 4) a suitable production media.

Recombinant AAV particles can be produced from packaging cell lysates. See, e.g., Chirico and Trempe (1998) *J. Virol. Methods* 76:31-41. However, the cell lysate contains various cellular components such as host cell DNA, host cell proteins, media components and either helper virus or helper virus plasmid DNA which must be separated from the rAAV vector before it is suitable for in vivo use. Recent advances in rAAV production include the use of non-adherent cell suspension processes in stirred tank bioreactors and production conditions whereby rAAV vectors are released into the media or supernatant reducing the concentration of host cellular components present in the production material but still containing appreciable amounts of in-process impurities. See U.S. Pat. No. 6,566,118 and PCT WO 99/11764. Therefore, rAAV particles may be collected from the media and/or cell lysate and further purified.

Methods including density gradient centrifugation employed for the purification of rAAV vectors and in particular rAAV-2 are not amenable to scale up. Recent reports for rAAV-2 vectors have described purification methods employing ion exchange chromatography including opposing ion exchange chromatography (including cation and anion chromatography). See for example U.S. Pat. No. 6,566,118 and PCT WO 99/11764 which disclose methods of using a combination of opposing ion exchange chromatography for purifying recombinant adeno-associated virus vectors from a culture supernatant and/or a cell lysate. Additional improvements in rAAV stock preparations include the use of deoxycholate treatment of the cell lysate, iodixanol gradient separation prior to the affinity chromatography, which have resulted in high titer rAAV2 (Clark et al., *Hum. Mol. Genet.* 10(6):1031-39 (1999); Zolotukhin et al., *Gene Therapy* 6(6):973-985 (1999)). O'Riordan et al. (O'Riordan et al., *J. Gene Med.* 2:444-454 (2000); U.S. Pat. No. 7,015,026) also reported scalable chromatographic purification process for recombinant adeno-associated virus vectors and as particularly exemplified, rAAV-2 vectors, using ion exchange chromatography, hydroxyapatite chromatography, cellufine sulfate affinity chromatography, and zinc chelate chromatography.

Recent data indicate that rAAV capsid serotypes such as rAAV-1, 4, 5, and 8 bind weakly to anionic resins either as purified virus stock or in the presence of in-process production impurities such as host cell DNA, host cell proteins, serum albumin, media components, and helper virus components. Consequently, purification of those capsid serotypes typically involves anion-exchange chromatography in combination with other purification methods, such as iodixinol density-gradient centrifugation. See, e.g., Zolotukhin et al., Methods 28(2):158-167 (2002) and Kaludov et al., *Hum. Gene Therapy* 13:1235-1243 (2002); and U.S. Patent Publication No. 2004/0110266 A1. However, those methods are not readily scalable to commercial scale processes.

Accordingly, in the development of recombinant AAV vectors such as those for use in gene therapy and gene vaccines, there is a need for methods of purifying rAAV vectors from in-process production components including helper virus, as well as helper virus proteins, cellular proteins, host cell DNA, and media components present in the rAAV production stock. Such methods should be effectively employed on a scale that is suitable for the practical application of gene therapy techniques. Moreover there is a need for development of purification processes for rAAV vectors that are scalable to yield high titer, highly purified commercial stocks useful for rAAV gene therapy and gene vaccines. More particularly, there is a need for development of purification processes for rAAV vectors that bind weakly to chromatographic resins and in particular anionic resins.

The disclosures of all publications, patent applications, and patents cited in this specification are herein incorporated by reference as if each individual publication, patent application, or patent were specifically and individually indicated to be incorporated by reference. In particular, all publications cited herein are expressly incorporated herein by reference for the purpose of describing and disclosing compositions and methods which might be used in connection with the invention. Although the invention provided herein has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

SUMMARY OF THE INVENTION

The invention provides methods of isolating a population of recombinant adeno-associated virus (rAAV) particles of any capsid serotype from in-process impurities by capturing the rAAV particles on an apatite chromatography medium in the presence of polyethylene glycol (PEG). The methods of the invention entail upstream processing (such as, for example, centrifugation, treatment with Benzonase®, anion exchange filtration, and/or tangential flow filtration) as well as downstream processing (such as, for example, heat inactivation, filtration, hydrophobic interaction chromatography, size exclusion chromatography, and/or anion exchange chromatography). The upstream and downstream methods may be used alone or in various combinations.

The invention provides methods for isolating a population of recombinant adeno-associated virus (rAAV) particles from in-process impurities in a feedstream, comprising the steps of: (a) contacting a feedstream containing the rAAV particles with an apatite chromatography medium in the presence of polyethylene glycol (PEG), wherein the rAAV particles bind to the apatite chromatography medium; and (b) eluting the rAAV particles bound to the apatite chromatography medium with an elution buffer containing less than 3% (w/v) PEG. In certain embodiments, the apatite chromatography medium is ceramic hydroxyapatite (CHT) or ceramic fluoroapatite (CFT). In certain embodiments, the rAAV particles bound to the apatite chromatography medium are eluted with an elution buffer containing less than 3% (w/v) PEG. In certain embodiments, the rAAV particles bound to the apatite chromatography medium are eluted with an elution buffer in the absence of PEG.

In some embodiments, the specific binding of the apatite chromatography medium is between $10^6$ and $10^{16}$ DNase-resistant particles (DRPs) per milliliter. In some embodiments, the specific binding of the apatite chromatography medium is between $10^8$ and $10^{16}$ DNase-resistant particles (DRPs) per milliliter. In some embodiments, the specific binding of the apatite chromatography medium is between $10^{10}$ and $10^{16}$ DNase-resistant particles (DRPs) per milliliter. In some embodiments, the specific binding of the apatite chromatography medium is between $10^{12}$ and $10^{16}$ DNase-resistant particles (DRPs) per milliliter. In some embodiments, the specific binding of the apatite chromatography medium is between $10^{14}$ and $10^{16}$ DNase-resistant particles (DRPs) per milliliter.

In some embodiments, the method further comprises an anion exchange filtration step before the apatite chromatography step, wherein the rAAV particles are in the flow-through of the anion exchange filtration. In some embodiments, the method further comprises concentrating the rAAV particles from the flow-through of the anion exchange filtration by tangential flow filtration before the apatite chromatography step. In some embodiments, the method further comprises a step of binding the rAAV particles in the feedstream eluted from the apatite chromatography medium to an anionic chromatography medium. In some embodiments, the method further comprises a step of heat inactivation step to inactivate the helper virus. In some embodiments, the method further comprises a step of binding the rAAV particles in the feedstream to a hydrophobic interaction chromatography after the apatite chromatography.

In some embodiments, the feedstream containing the rAAV particles is contacted with an apatite chromatography medium in the presence of polyethylene glycol (PEG) and a basic buffer. In some embodiments, the basic buffer is between pH 7.2 and 10, between pH 7.4 and 10, between pH 7.6 and 10, between pH 7.8 and 10, between pH 8.0 and 10.0, between pH 8.2 and 10.0, between pH 8.4 and 10.0, between pH 8.6 and 10.0, between pH 8.8 and 10, between pH 9.0 and 10.0, between pH 9.2 and 10, between pH 9.4 and 10.0, between pH 9.6 and 10.0, or between pH 9.8 and 10.0. In some embodiments, the basic buffer has a pH of about any of 7.2, 7.6, 7.8, 8.0, 8.2, 8.4, 8.6, 8.8, 9.0, 9.2, 9.4, 9.6, 9.8, and 10.0. Any basic buffer known in the art may be used. In some embodiments, the basic buffer comprises borate. In some embodiments, the basic buffer is borate.

In some embodiments, the feedstream containing the rAAV particles is contacted with an apatite chromatography medium in the presence of polyethylene glycol (PEG). For example, between about 3% (w/v) and about 10% (w/v) of PEG may be used. In some embodiments, the feedstream containing the rAAV particles is contacted with an apatite chromatography medium in the presence of about 3% (w/v), about 3.5% (w/v), about 4% (w/v), about 4.5% (w/v), about 5% (w/v), about 5.5% (w/v), about 6% (w/v), about 6.5% (w/v), about 7% (w/v), about 7.5% (w/v), about 8% (w/v), about 8.5% (w/v), about 9% (w/v), about 9.5% (w/v), or about 10% (w/v) PEG.

In some embodiments, the PEG has an average molecular weight between about 5,000 (PEG5000) grams per mole and about 15,000 (PEG15000) grams per mole, such as, about 5,000 grams per mole (PEG5000), about 6,000 (PEG6000) grams per mole, about 7,000 (PEG7000) grams per mole, about 8,000 (PEG8000) grams per mole, about 9,000 (PEG9000) grams per mole, about 10,000 (PEG10000) grams per mole, about 11,000 (PEG11000) grams per mole, about 12,000 (PEG12000) grams per mole, about 13,000 (PEG13000) grams per mole, about 14,000 (PEG14000) grams per mole, and about 15,000 (PEG15000) grams per mole. In certain embodiments, the PEG has an average molecular weight of about 5,000 (PEG5000) grams per mole. In certain embodiments, the PEG has an average molecular weight of about 6,000 (PEG6000) grams per mole. In certain embodiments, the PEG has an average molecular weight of about 8,000 (PEG8000) grams per mole. In certain embodiments, the PEG has an average molecular weight of about 10,000 (PEG10000) grams per mole. In certain embodiments, the PEG has an average molecular weight of about 15,000 (PEG15000) grams per mole.

In some embodiments, the feedstream containing the rAAV particles is contacted with an apatite chromatography medium in the presence of between about 3% (w/v) and about 10% (w/v) PEG6000. In some embodiments, the feedstream containing the rAAV particles is contacted with an apatite chromatography medium in the presence of about 3% (w/v) PEG6000. In some embodiments, the feedstream containing the rAAV particles is contacted with an apatite chromatography medium in the presence of about 4% (w/v) PEG6000. In some embodiments, the feedstream containing the rAAV particles is contacted with an apatite chromatography medium in the presence of about 5% (w/v) PEG6000. In some embodiments, the feedstream containing the rAAV particles is contacted with an apatite chromatography medium in the presence of about 6% (w/v) PEG6000. In some embodiments, the feedstream containing the rAAV particles is contacted with an apatite chromatography medium in the presence of about 7% (w/v) PEG6000. In some embodiments, the feedstream containing the rAAV particles is contacted with an apatite chromatography medium in the presence of about 8% (w/v) PEG6000. In some embodiments, the feedstream containing the rAAV particles is contacted with an apatite chromatography medium in the presence of about 9% (w/v) PEG6000. In some embodiments, the feedstream containing the rAAV particles is contacted with an apatite chromatography medium in the presence of about 10% (w/v) PEG6000.

In some embodiments, the feedstream containing the rAAV particles is contacted with an apatite chromatography medium in the presence of between about 3% (w/v) and about 10% (w/v) PEG8000. In some embodiments, the feedstream containing the rAAV particles is contacted with an apatite chromatography medium in the presence of about 3% (w/v) PEG8000. In some embodiments, the feedstream containing the rAAV particles is contacted with an apatite chromatography medium in the presence of about 4% (w/v) PEG8000. In some embodiments, the feedstream containing the rAAV particles is contacted with an apatite chromatography medium in the presence of about 5% (w/v) PEG8000. In some embodiments, the feedstream containing the rAAV particles is contacted with an apatite chromatography medium in the presence of about 6% (w/v) PEG8000. In some embodiments, the feedstream containing the rAAV particles is contacted with an apatite chromatography medium in the presence of about 7% (w/v) PEG8000. In some embodiments, the feedstream containing the rAAV particles is contacted with an apatite chromatography medium in the presence of about 8% (w/v) PEG8000. In some embodiments, the feedstream containing the rAAV particles is contacted with an apatite chromatography medium in the presence of about 9% (w/v) PEG8000. In some embodiments, the feedstream containing the rAAV particles is contacted with an apatite chromatography medium in the presence of about 10% (w/v) PEG8000.

In some embodiments, the feedstream containing the rAAV particles is contacted with an apatite chromatography medium in the presence of between about 3% (w/v) and about 10% (w/v) PEG10000. In some embodiments, the feedstream containing the rAAV particles is contacted with an apatite chromatography medium in the presence of about 3% (w/v) PEG10000. In some embodiments, the feedstream containing the rAAV particles is contacted with an apatite chromatography medium in the presence of about 4% (w/v) PEG10000. In some embodiments, the feedstream containing the rAAV particles is contacted with an apatite chromatography medium in the presence of about 5% (w/v) PEG10000. In some embodiments, the feedstream containing the rAAV particles is contacted with an apatite chromatography medium in the presence of about 6% (w/v) PEG10000. In some embodiments, the feedstream containing the rAAV particles is contacted with an apatite chromatography medium in the presence of about 7% (w/v) PEG10000. In some embodiments, the feedstream containing the rAAV particles is contacted with an apatite chromatography medium in the presence of about 8% (w/v) PEG10000. In some embodiments, the feedstream containing the rAAV particles is contacted with an apatite chromatography medium in the presence of about 9% (w/v) PEG10000. In some embodiments, the feedstream containing the rAAV particles is contacted with an apatite chromatography medium in the presence of about 10% (w/v) PEG10000.

In some embodiments, the feedstream containing the rAAV particles is contacted with an apatite chromatography medium in the presence of between about 3% (w/v) and about 10% (w/v) PEG15000. In some embodiments, the feedstream containing the rAAV particles is contacted with an apatite chromatography medium in the presence of about 3% (w/v) PEG15000. In some embodiments, the feedstream containing the rAAV particles is contacted with an apatite chromatography medium in the presence of about 4% (w/v) PEG15000. In some embodiments, the feedstream containing the rAAV particles is contacted with an apatite chromatography medium in the presence of about 5% (w/v) PEG15000. In some embodiments, the feedstream containing the rAAV particles is contacted with an apatite chromatography medium in the presence of about 6% (w/v) PEG15000. In some embodiments, the feedstream containing the rAAV particles is contacted with an apatite chromatography medium in the presence of about 7% (w/v) PEG15000. In some embodiments, the feedstream containing the rAAV particles is contacted with an apatite chromatography medium in the presence of about 8% (w/v)

PEG15000. In some embodiments, the feedstream containing the rAAV particles is contacted with an apatite chromatography medium in the presence of about 9% (w/v) PEG15000. In some embodiments, the feedstream containing the rAAV particles is contacted with an apatite chromatography medium in the presence of about 10% (w/v) PEG15000.

In some embodiments, the feedstream containing the rAAV particles is contacted with an apatite chromatography medium in a buffer comprising about 20 mM borate pH 9.0, and about 5% PEG (such as PEG6000). In some embodiments, the feedstream is mixed in-line with an equal volume of a buffer comprising about 40 mM borate at pH 9.0 and about 10% PEG to yield a final concentration of about 20 mM borate at pH 9.0 and about 5% PEG.

In some embodiments, the apatite chromatography medium with the rAAV particles bound to the medium is washed to remove the in-process impurities before eluting the rAAV particles. In some embodiments, the apatite chromatography medium is washed one or more times with a wash buffer containing decreasing concentrations of PEG to remove the in-process impurities. In some embodiments, the apatite chromatography medium is washed one or more times with a wash buffer containing between about 3% (w/v) and about 10% (w/v) PEG. In some embodiments, the wash buffer contains about any of 10% (w/v), 9.5% (w/v), 9% (w/v), 8.5% (w/v), 8% (w/v), 7.5% (w/v), 7% (w/v), 6.5% (w/v), 6% (w/v), 5.5% (w/v), 5% (w/v), 4.5% (w/v), 4% (w/v), 3.5% (w/v), and 3% (w/v) PEG. In some embodiments, the apatite chromatography medium is washed one or more times with a wash buffer containing 7.5% (w/v) PEG6000. In some embodiments, the apatite chromatography medium is washed one or more times with a wash buffer containing 7.5% (w/v) PEG8000. In some embodiments, the apatite chromatography medium is washed one or more times with a wash buffer containing 7.5% (w/v) PEG10000. In some embodiments, the apatite chromatography medium is washed one or more times with a wash buffer containing 7.5% (w/v) PEG15000. In some embodiments, the apatite chromatography medium is washed one or more times with a wash buffer containing about 5% (w/v) PEG6000. In some embodiments, the apatite chromatography medium is washed one or more times with a wash buffer containing about 5% (w/v) PEG8000. In some embodiments, the apatite chromatography medium is washed one or more times with a wash buffer containing about 5% (w/v) PEG10000. In some embodiments, the apatite chromatography medium is washed one or more times with a wash buffer containing about 5% (w/v) PEG15000. In some embodiments, the apatite chromatography medium is washed one or more times with a wash buffer containing less than about 3% (w/v) PEG6000. In some embodiments, the apatite chromatography medium is washed one or more times with a wash buffer containing less than about 3% (w/v) PEG8000. In some embodiments, the apatite chromatography medium is washed one or more times with a wash buffer containing less than about 3% (w/v) PEG10000. In some embodiments, the apatite chromatography medium is washed one or more times with awash buffer containing less than about 3% (w/v) PEG15000. In some embodiments, the apatite chromatography medium is washed one or more times with a wash buffer containing no PEG.

In some embodiments, the wash buffer contains buffers known in the art. In some embodiment, the wash buffer comprises a buffer selected from the group consisting of borate, N-2-Hydroxyethylpiperazine-N'-2-ethanesulfonic acid (HEPES), and Tris-HC. In some embodiments, the wash buffer comprises or is borate. In some embodiments, the wash buffer comprises or is HEPES. In some embodiments, the wash buffer comprises or is Tris-HCl. In some embodiments, the wash buffer is at basic pH. In some embodiments, the wash buffer has a pH between pH 7.0 and pH 10.0, between pH 7.2 and pH 10.0, between pH 7.4 and pH 10.0, between pH 7.6 and pH 10.0, between pH 7.8 and pH 10.0, pH 8.0 and pH 10.0, pH 8.2 and pH 10.0, between pH 8.4 and pH 10.0, between pH 8.6 and pH 10.0, between pH 8.8 and pH 10.0, between pH 9.0 and pH 10.0, between pH 9.2 and pH 10.0, between pH 9.4 and pH 10.0, between pH 9.6 and pH 10.0, or between pH 9.8 and pH 10.0. In some embodiments, the wash buffer has a pH at 7.0, 7.2, 7.4, 7.6, 7.8, 8.0, 8.2, 8.4, 8.6, 8.8, 9.0, 9.2, 9.4, 9.6, 9.8, or 10.0. In some embodiments, the wash buffer comprises or is borate at a pH between 8.0 and 10.0. In some embodiments, the wash buffer comprises or is borate at pH 8.0. In some embodiments, the wash buffer comprises or is borate at pH 9.0. In some embodiments, the wash buffer comprises or is borate at pH 10.0. In some embodiments, the wash buffer comprises or is HEPES at a pH between 7.0 and 10.0. In some embodiments, the wash buffer comprises or is HEPES at pH 7.0. In some embodiments, the wash buffer comprises or is HEPES at pH 8.0. In some embodiments, the wash buffer comprises or is HEPES at pH 9.0. In some embodiments, the wash buffer comprises or is HEPES at pH 10.0. In some embodiments, the wash buffer comprises or is Tris-HCl at a pH between 7.0 and 10.0. In some embodiments, the wash buffer comprises or is Tris-HCl at pH 7.0. In some embodiments, the wash buffer comprises or is Tris-HCl at pH 8.0. In some embodiments, the wash buffer comprises or is Tris-HCl at pH 9.0. In some embodiments, the wash buffer comprises or is Tris-HCl at pH 10.0. In some embodiments, the wash buffer further comprises between 100 and 500 mM phosphate. In some embodiments, the wash buffer further comprises between 50 and 250 mM NaCl.

In some embodiments, the wash step comprises a first wash with a wash buffer comprising about 30 mM borate at pH about 9.0 and about 7.5% PEG; a second wash with a wash buffer comprising about 150 potassium phosphate, about 20 mM borate at pH about 9.0, and about 5% PEG; a third wash with a wash buffer comprising about 20 mM borate at pH about 9.0 and about 5% PEG; and a fourth wash with a wash buffer comprising about 20 mM HEPES at pH about 7.0 and 150 mM NaCl.

In some embodiments, the rAAV particles bound to the apatite chromatography medium are eluted with an elution buffer containing low concentrations of PEG or in the absence of PEG. In some embodiments, the elution buffer contains less than about 3% (w/v) PEG, less than about 2% (w/v) PEG, or less than about 1% (w/v) PEG. In some embodiments, the elution buffer contains about 2.5% (w/v), about 2% (w/v), about 1.5% (w/v), about 1% (w/v), or about 0.5% (w/v) PEG, or no PEG. In some embodiments, the elution buffer contains less than about 3% (w/v) PEG6000. In some embodiments, the elution buffer contains less than about 3% (w/v) PEG8000. In some embodiments, the elution buffer contains less than about 3% (w/v) PEG10000. In some embodiments, the elution buffer contains less than about 3% (w/v) PEG15000. In some embodiments, the rAAV particles bound to the apatite chromatography medium are eluted with an elution buffer in the absence of PEG. In some embodiments, the elution buffer comprises a buffer selected from the group consisting of borate, N-2-Hydroxyethylpiperazine-N'-2-ethanesulfonic acid (HEPES), and Tris-HC. In some embodiments, the elution buffer comprises or is borate. In some embodiments, the elution buffer comprises or is HEPES. In some embodiments, the elution buffer comprises or is Tris-HCl. In some embodiments, the elution buffer is at neutral pH. In some embodiments, the elution buffer comprises or is HEPES at neutral pH. In some embodiments, the elution buffer comprises or is Tris-HCl at neutral pH. In some embodiments, the elution buffer further comprises less than 100 mM phosphate. In some embodiments, the elution buffer further comprises less than 50 mM phosphate. In some embodiments, the elution buffer further comprises between 50 and 250 mM NaCl. In some embodiments, the rAAV particles bound to the apatite chromatography medium are eluted with an elution buffer comprising about 50 mM potassium phosphate, about 20 mM HEPES at pH about 7.0, and about 150 mM NaCl.

In some embodiments, the method od isolating the rAAV particles from in-process impurities in a feedstream comprising the steps of: (a) contacting a feedstream containing the rAAV particles with an apatite chromatography medium in the presence of about 5% (w/v) PEG in a basic buffer at pH about 9.0, wherein the rAAV particles bind to the apatite chromatography medium; (b) washing the apatite chromatography medium with a first wash buffer comprising about 30 mM borate at pH about 9.0 and about 7.5% PEG; (c) washing the apatite chromatography medium with a second wash buffer comprising about 150 potassium phosphate, about 20 mM borate at pH about 9.0, and about 5% PEG; (d) washing the apatite chromatography medium with a third wash buffer comprising about 20 mM borate at pH about 9.0 and about 5% PEG; (e) washing the apatite chromatography medium with a fourth wash buffer comprising about 20 mM HEPES at pH about 7.0 and 150 mM NaCl; and (f) eluting the rAAV particles bound to the apatite chromatography medium with an elution buffer comprising about 50 mM potassium phosphate, about 20 mM HEPES at pH about 7.0, and about 150 mM NaCl.

Also provided herein are methods for isolating a population of recombinant adeno-associated virus (rAAV) particles from in-process impurities in a feedstream, comprising the steps of: (a) contacting a feedstream containing the rAAV particles with a hydrophobic interaction chromatography (HIC) medium in a high salt buffer, wherein the rAAV particles and the in-process impurities bind the HIC medium; and (b) eluting the rAAV particles bound to the HIC medium with a medium salt buffer. In some embodiments, the HIC medium is selected from the group consisting of Tosoh Butyl 650M, Tosoh SuperButyl 650C, Tosoh Phenyl 650C, EMD Fractogel Phenyl, and Tosoh Has(butyl) resin. In some embodiments, the high salt buffer comprises or is between 0.5 M and 2.0 M citrate (e.g., sodium citrate). In some embodiments, the high salt buffer comprises about any of 0.5 M, 0.75 M, 1.0 M, 1.25 M, 1.5 M, 1.75 M, and 2.0 M citrate. In some embodiments, the medium salt buffer comprises or is less than 0.5 M citrate (e.g., sodium citrate). In some embodiments, the medium salt buffer comprising between 0.5 M to about 0.3 M citrate. In some embodiments, the medium salt buffer comprises about any of 0.45 M, 0.4 M, 0.35 M, 0.3 M, and 0.25 M of citrate. In some embodiments, the high salt buffer further comprises between 1 and 100 mM phosphate. In some embodiments, the medium salt buffer further comprises between 1 and 100 mM phosphate. In some embodiments, the medium salt buffer elutes the rAAV particles without eluting rAAV particles with empty capsids, partially denatured capsids, less infectious capsids, and/or partially full capsids.

In any of the embodiments described herein, the rAAV particles have an AAV capsid serotype selected from the group consisting of AAV-1, AAV-2, AAV-3, AAV-4, AAV-5, AAV-6, AAV-7, AAV-8, AAV-9, AAV-10, AAV-11, AAV-12, AAV-13, AAV-14, AAV-15 and AAV-16. In some embodiments, the rAAV particles have an AAV capsid serotype selected from the group consisting of AAV-1, AAV-4, AAV-5, and AAV-8. In some embodiments, the rAAV particles have an AAV capsid serotype of AAV-1. In some embodiments, the rAAV particles have an AAV capsid serotype of AAV-4. In some embodiments, the rAAV particles have an AAV capsid serotype of AAV-5. In some embodiments, the rAAV particles have an AAV capsid serotype of AAV-8. In some embodiments, the rAAV particles comprise an AAV capsid protein from an AAV serotype selected from the group consisting of AAV-1, AAV-2, AAV-3, AAV-4, AAV-5, AAV-6, AAV-7, AAV-8, AAV-9, AAV-10, AAV-11, AAV-12, AAV-13, AAV-14, AAV-15 and AAV-16. In some embodiments, the rAAV particles have an AAV capsid serotype that is a weak anionic binder. In some embodiments, the AAV capsid serotype that is a weak anionic binding is selected from the group consisting of AAV-1, AAV-4, AAV-5, and AAV-8. In some embodiments, the composition containing rAAV particles further comprises production culture contaminants. In some embodiments, the production culture contaminants comprise damaged rAAV particles, host cell contaminants, helper virus contaminants, and/or cell culture contaminants. In some embodiments, the host cell contaminants comprise host cell DNA, plasmids, or host cell protein. In some embodiments, the helper virus contaminants comprise adenovirus particles, adenovirus DNA, or adenovirus proteins. In some embodiments, the cell culture contaminants comprise media components, serum albumin, or other serum proteins. In some embodiments, the cell culture contaminants comprise media components. In some embodiments, the cell culture contaminants do not comprise serum albumin or other serum proteins.

It is to be understood that one, some, or all of the properties of the various embodiments described herein may be combined to form other embodiments of the present invention.

BRIEF DESCRIPTION OF THE FIGURES

FIG. 1 presents the results of Benzonase® digestion of the clarified supernatant from rAAV production culture harvest. The results demonstrate that no high molecular weight DNA was present following Benzonase® digestion.

DETAILED DESCRIPTION

Figure 2:
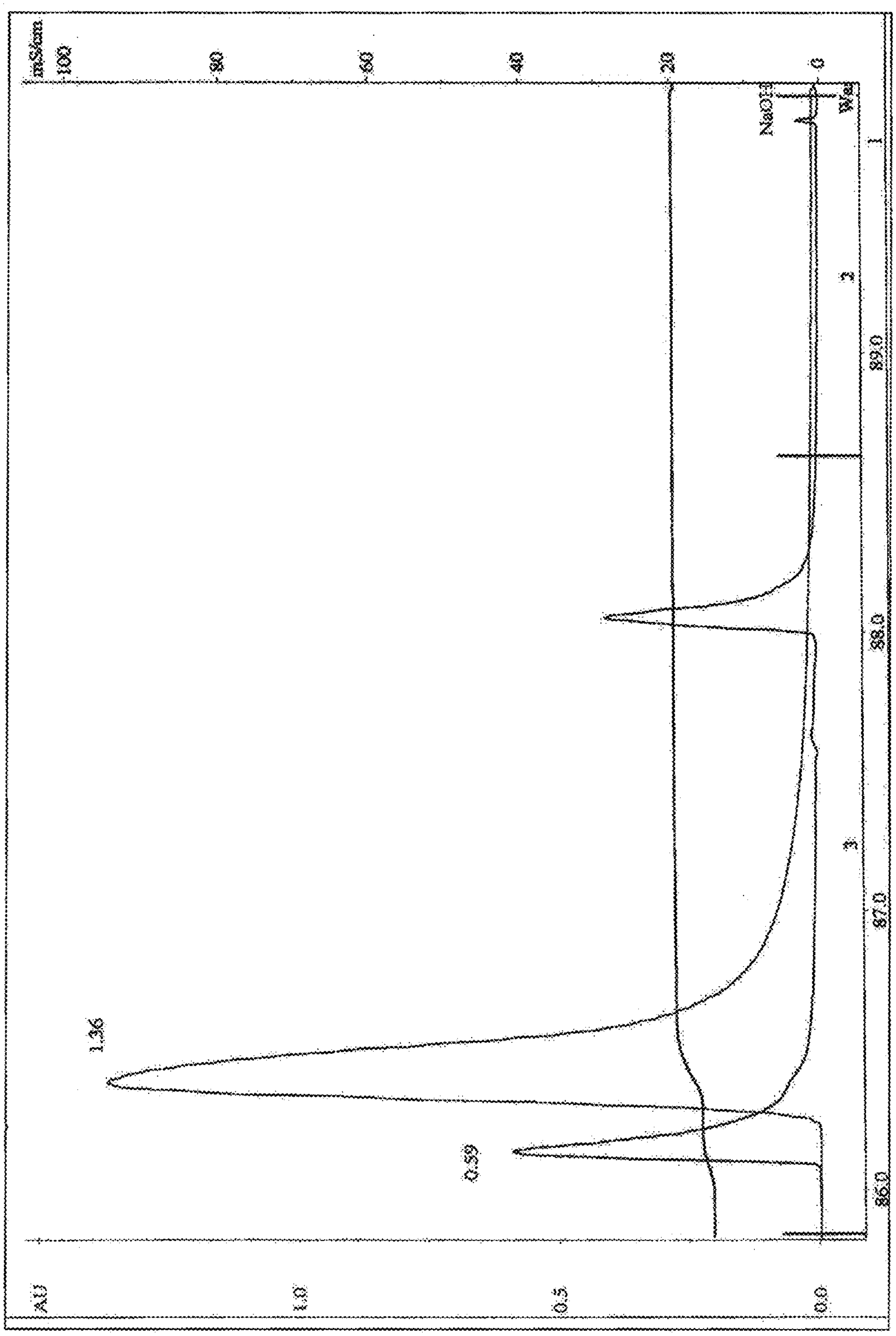
FIG. 2 presents a typical spectrophotometric tracing for a typical resin screened for rAAV binding affinity as described in Example 4. Absorbance (AU) and conductivity (mS/cm) were indicated.

It is an object of this invention to provide methods for isolating a population of recombinant adeno-associated virus (rAAV) particles of any AAV capsid serotype from production culture contaminants such as damaged rAAV particles, helper virus, helper virus proteins, plasmids, cellular proteins and DNA, media components, serum proteins, and the like. Furthermore, the methods of the present invention provide commercially scalable, orthogonal processes consistent with regulatory requirements for isolation of a population of rAAV particles from high titer rAAV production culture harvests or feedstreams. The populations of rAAV particles isolated by the methods of the present invention are substantially free of contaminants, including production culture contaminants and/or in-process contaminants, such as damaged rAAV particles, helper virus, helper virus proteins, plasmids, cellular proteins and DNA, media components, serum proteins and glucans. The methods of the present invention are particularly suited to rAAV vector serotypes which are weak anionic binders such as, for example, rAAV-1, rAAV-4, rAAV-5, and rAAV-8. The invention further contemplates a method for isolating a high titer population of rAAV particles substantially free of contaminants, including production culture contaminants and/or in-process contaminants, suitable for use in gene therapy applications without the need for performing density gradient centrifugation.

Definitions

The term "isolated" or "purified" as used herein refers to a preparation of rAAV particles devoid of at least some of the other components that may also be present where the rAAV particles naturally occur or are initially prepared from. Thus, for example, isolated rAAV particles may be prepared using a purification technique to enrich it from a source mixture, such as a culture lysate or production culture supernatant. Enrichment can be measured in a variety of ways, such as, for example, by the proportion of DNase-resistant particles (DRPs) present in a solution, or by infectivity, or it can be measured in relation to a second, potentially interfering substance present in the source mixture, such as contaminants, including production culture contaminants or in-process contaminants, including helper virus, media components, and the like, as defined below.

A preparation of rAAV is said to be "substantially free" of helper virus if the ratio of infectious AAV particles to infectious helper virus particles is at least about $10^2$:1; preferably at least about $10^4$:1, more preferably at least about $10^6$:1; still more preferably at least about $10^8$:1. Preparations are also preferably free of equivalent amounts of helper virus proteins (i.e., proteins as would be present as a result of such a level of helper virus if the helper virus particle impurities noted above were present in disrupted form). Viral and/or cellular protein contamination can generally be observed as the presence of Coomassie staining bands on SDS gels (e.g., the appearance of bands other than those corresponding to the AAV capsid proteins VP1, VP2 and VP3).

The term "weak anionic binder" or "low affinity anionic binder" as used herein interchangeably refers to an rAAV particle having a capsid serotype which, in the presence of contaminants (including production culture contaminants or in-process contaminants), does not bind with sufficient affinity to allow for isolation of the rAAV particles from other rAAV production culture contaminants. Such capsid serotypes are known in the art and include, without limitation, AAV-1, AAV-5, AAV-8 and AAV-4. As described in the art, such weak anionic binders are generally purified by methods that include at least one density centrifugation step including iodixinol (sold under the trade name Optiprep®) or cesium chloride gradient centrifugation.

As used herein, the term "helper virus" or "contaminating helper virus" refers to a virus used when producing copies of a helper virus-dependent viral vector, such as adeno-associated virus, which does not have the ability to replicate on its own. The helper virus is used to co-infect cells alongside the viral vector and provides the necessary proteins for replication of the genome of the viral vector. The term encompasses intact viral particles, empty capsids, viral DNA and the like. Helper viruses commonly used to produce rAAV particles include adenovirus, herpes simplex virus, cytomegalovirus, Epstein-Barr virus, and vaccinia virus.

The term "production culture" as used herein refers to a vessel containing the necessary components for rAAV vector particle production. Production cultures include, without limitation, the following components: 1) a suitable host cell; 2) helper virus function; 3) AAV rep and cap genes and gene products; 4) the therapeutic transgene flanked by AAV ITR sequences; and 5) suitable media, media components, and media supplements, including without limitation serum, serum-derived proteins, vitamins, essential and non-essential amino acids, and glucose known to support rAAV production.

As used herein, the terms "contaminants," "production culture contaminants," "in-process contaminants," "in-process impurities," "impurities," or "contaminants," as used interchangeably herein, refer to, without limitation, media formulations known in the art to support production of rAAV vectors; media supplements such as salts, calf serum, amino acid supplements, vitamin supplements, growth factors, serum albumin and other low molecular weight proteins present in media formulations know in the art; permissive host cells, host cell proteins or host cell DNA; helper viruses, helper virus proteins, or helper virus DNA such as wild type adenovirus or herpes virus proteins; and other non rAAV vector or rAAV vector production culture materials introduced during the purification process such as glucans or chromatography buffers utilized in the purification of rAAV vectors from feedstreams.

The term "production culture harvest" as used herein is defined as a solution comprising rAAV vector particles produced from rAAV vector production cultures by means known in the art, including without limitation transfection processes, stable cell line production, Ad-hybrid production systems, or baculovirus production systems. Furthermore, the term "production culture harvest" as used herein refers to the material isolated from the production culture vessel and includes both materials isolated by lysis of rAAV producer cells by means known in the art and materials isolated from rAAV production cultures maintained under culture conditions known in the art to yield rAAV particles released into the media from intact cells. A production culture harvest may contain some or all of the following, without limitation: rAAV vector particles, production culture components, such as, media components, host cell proteins, host cell DNA, host cells, helper virus, helper virus proteins, helper virus DNA, plasmid DNA, carrier virus DNA, serum, serum-derived proteins and media supplements.

The term "feedstream" as used herein refers to a source of rAAV vector particles that is loaded onto, passed through, or applied to a chromatographic matrix. Feedstreams of the present invention include production culture harvests, and materials isolated from previous chromatographic steps of the invention whether the material was present as flow-through from the previous step, bound and eluted in the previous step, present in the void volume of the previous step or present in any fraction obtained during the purification of rAAV particles. Such feedstreams may include one or more "contaminants," "production culture contaminants," "in-process contaminants," "in-process impurities," or "impurities," or "contaminants," as defined herein.

The terms "capture," "bound," "binds," or "binding" as used herein interchangeably refer to the binding, adherence or sticking of a component of a feedstream to a chromatographic medium. Components may be bound to a chromatographic medium by any force or chemistry known in the art, including without limitation hydrophobic, ionic (including anionic and cationic), affinity, metal chelation, and chelation. Components may be bound to a chromatographic medium by more than one type of chemistry such as in apatite chromatographic media.

The terms "apatite resin," "apatite chromatographic medium," "apatite matrix" or "apatite medium," as used herein interchangeably refer to a chromatographic medium comprised of a mineral of calcium phosphate, and includes without limitation ceramic hydroxyapatite (CHT) and ceramic fluoroapatite (CFT) chromatographic media.

The terms "mixed mode" or "multimodal" refer to chromatographic media which have the capacity for more than one binding chemistry. Mixed mode chromatographic media include without limitation apatite chromatographic media, which are capable of exhibiting metal affinity binding via the calcium moieties, hydrogen bonding via the hydroxyl groups present on the backbone, positive charge repulsion and negative charge attraction via the calcium moieties and negative charge repulsion and positive charge attraction via the phosphate moieties present on the media.

General reference to "the composition" or "compositions" includes and is applicable to compositions of the invention.

As used herein, the singular form of the articles "a," "an," and "the" includes plural references unless indicated otherwise. For example, the phrase "a virus particle" includes one or more virus particles.

Reference to "about" a value or parameter herein includes (and describes) embodiments that are directed to that value or parameter per se. For example, description referring to "about X" includes description of "X."

It is understood that aspects and embodiments of the invention described herein include consisting and/or consisting essentially of aspects and embodiments.

Production of rAAV Vectors

Numerous methods are known in the art for production of rAAV vectors, including transfection, stable cell line production, and infectious hybrid virus production systems which include Adenovirus-AAV hybrids, herpesvirus-AAV hybrids and baculovirus-AAV hybrids. rAAV production cultures for the production of rAAV virus particles all require; 1) suitable host cells, including, for example, human-derived cell lines such as HeLa, A549, or 293 cells, or insect-derived cell lines such as SF-9, in the case of baculovirus production systems; 2) suitable helper virus function, provided by wild type or mutant adenovirus (such as temperature sensitive adenovirus), herpes virus, baculovirus, or a plasmid construct providing helper functions; 3) AAV rep and cap genes and gene products; 4) a transgene (such as a therapeutic transgene) flanked by AAV ITR sequences; and 5) suitable media and media components to support rAAV production. Suitable media known in the art may be used for the production of rAAV vectors. These media include, without limitation, media produced by Hyclone Laboratories and JRH including Modified Eagle Medium (MEM), Dulbecco's Modified Eagle Medium (DMEM), custom formulations such as those described in U.S. Pat. No. 6,566,118, and Sf-900 II SFM media as described in U.S. Pat. No. 6,723,551, each of which is incorporated herein by reference in its entirety, particularly with respect to custom media formulations for use in production of recombinant AAV vectors.

Suitable rAAV production culture media of the present invention may be supplemented with serum or serum-derived recombinant proteins at a level of 0.5%-20% (v/v or w/v). Alternatively, as is known in the art, rAAV vectors may be produced in serum-free conditions which may also be referred to as media with no animal-derived products. One of ordinary skill in the art may appreciate that commercial or custom media designed to support production of rAAV vectors may also be supplemented with one or more cell culture components know in the art, including without limitation glucose, vitamins, amino acids, and or growth factors, in order to increase the titer of rAAV in production cultures.

rAAV production cultures can be grown under a variety of conditions (over a wide temperature range, for varying lengths of time, and the like) suitable to the particular host cell being utilized. As is known in the art, rAAV production cultures include attachment-dependent cultures which can be cultured in suitable attachment-dependent vessels such as, for example, roller bottles, hollow fiber filters, micro-carriers, and packed-bed or fluidized-bed bioreactors. rAAV vector production cultures may also include suspension-adapted host cells such as HeLa, 293, and SF-9 cells which can be cultured in a variety of ways including, for example, spinner flasks, stirred tank bioreactors, and disposable systems such as the Wave bag system.

rAAV vector particles of the invention may be harvested from rAAV production cultures by lysis of the host cells of the production culture or by harvest of the spent media from the production culture, provided the cells are cultured under conditions known in the art to cause release of rAAV particles into the media from intact cells, as described more fully in U.S. Pat. No. 6,566,118). Suitable methods of lysing cells are also known in the art and include for example multiple freeze/thaw cycles, sonication, microfluidization, and treatment with chemicals, such as detergents and/or proteases.

Purification of rAAV Vectors

At harvest, rAAV production cultures of the present invention may contain one or more of the following: (1) host cell proteins; (2) host cell DNA; (3) plasmid DNA; (4) helper virus; (5) helper virus proteins; (6) helper virus DNA; and (7) media components including, for example, serum proteins, amino acids, transferrins and other low molecular weight proteins. In addition, rAAV production cultures further include rAAV particles having an AAV capsid serotype selected from the group consisting of AAV-1, AAV-2, AAV-3, AAV-4, AAV-5, AAV-6, AAV-7, AAV-8, AAV-9, AAV-10, AAV-11, AAV-12, AAV-13, AAV-14, AAV-15 and AAV-16. In some embodiments, the rAAV particles have an AAV capsid serotype selected from the group consisting of AAV-1, AAV-4, AAV-5, and AAV-8.

In some embodiments, the rAAV production culture harvest is clarified to remove host cell debris. In some embodiments, the production culture harvest is clarified by filtration through a series of depth filters including, for example, a grade D0HC Millipore Millistak+ HC Pod Filter, a grade A1HC Millipore Millistak+ HC Pod Filter, and a 0.2 μm Filter Opticap XL10 Millipore Express SHC Hydrophilic Membrane filter. Clarification can also be achieved by a variety of other standard techniques known in the art, such as, centrifugation or filtration through any cellulose acetate filter of 0.2 μm or greater pore size known in the art.

In some embodiments, the rAAV production culture harvest is further treated with Benzonase® to digest any high molecular weight DNA present in the production culture. In some embodiments, the Benzonase® digestion is performed under standard conditions known in the art including, for example, a final concentration of 1-2.5 units/ml of Benzonase® at a temperature ranging from ambient to 37° C. for a period of 30 minutes to several hours.

rAAV particles may be isolated or purified using one or more of the following purification steps: flow-through anionic exchange filtration, tangential flow filtration (TFF) for concentrating the rAAV particles, rAAV capture by apatite chromatography, heat inactivation of helper virus, rAAV capture by hydrophobic interaction chromatography, buffer exchange by size exclusion chromatography (SEC), nanofiltration, and rAAV capture by anionic exchange chromatography. These steps may be used alone, in various combinations, or in different orders. In some embodiments, the method comprises all the steps in the order as described below.

Anionic Exchange Filtration

Optionally in some embodiments, the clarified and Benzonase®-treated production culture harvest is subjected to anionic exchange filtration under conditions where the rAAV vector is present in the flow-through and contaminating helper virus is retained on the charged filter. At the ionic strength of the rAAV production culture harvest, the rAAV particles can be distinguished from helper virus, for example, adenovirus by passage through an anionic filter such as a Mustang® Q filter (Pall Corp., East Hills, NY). One skilled in the art can determine the size and number of filters necessary to achieve the optimal log reduction of adenovirus (LRV) and adenoviral proteins present in the clarified, Benzonase®-treated and anionic filtered production culture. In some embodiments, the LRV is at least one log and greater than ten logs. In a preferred embodiment, the LRV is at least two and greater than eight logs. In a more preferred embodiment the LRV is at least six logs.

Tangential Flow Filtration (TFF) Concentration

In some embodiments, the flow-through from the anionic filtration of the clarified, Benzonase®-treated feedstream is concentrated via tangential flow filtration ("TFF") before being applied to an apatite chromatographic medium. Large scale concentration of viruses using TFF ultrafiltration has been described by R. Paul et al., Human Gene Therapy, 4:609-615 (1993). TFF concentration of the feedstream enables a technically manageable volume of feedstream to be subjected to the chromatography steps of the present invention and allows for more reasonable sizing of columns without the need for lengthy recirculation times. In some embodiments, the rAAV feedstream is concentrated between at least two-fold and at least ten-fold. In some embodiments, the feedstream is concentrated between at least ten-fold and at least twenty-fold. In some embodiments, the feedstream is concentrated between at least twenty-fold and at least fifty-fold. One of ordinary skill in the art will also recognize that TFF can also be used at any step in the purification process where it is desirable to exchange buffers before performing the next step in the purification process.

rAAV Capture by Apatite Chromatography in the Presence of Polyethylene Glycol (PEG)

FDA-approved processes for purification of proteins and other biologic products suitable for use in human clinical trials and pharmaceutical products rely upon commercial scale orthogonal processes. A multi-step purification scheme is considered to include an orthogonal process if it employs separation mechanisms that are distinct from one another, with each step representing an axis in Cartesian space. For example, a two-step process using anion exchange and hydrophobic interaction chromatography (HIC) would be considered orthogonal. The processes for removing contaminants, such as production culture contaminants or in-process contaminants, from a production culture harvest or feedstream described herein are orthogonal processes including both capture and flow-through steps on a variety of chromatographic media for the final product (i.e., an rAAV vector). rAAV vectors (specifically rAAV-2) have been demonstrated in the art to bind anionic resins. rAAV vectors such as rAAV-1, -5, and -8 have been demonstrated to bind much less tightly than rAAV-2 to anionic exchange media in the presence of production components such as serum albumin, helper virus components, production media components and host cell DNA, resulting in a less efficient and lower quality purification scheme.

Previous purification strategies described in the art for lower affinity anionic binders such as AAV-1 included an iodixinol step gradient which reduces the relative concentration of the contaminants, such as production culture contaminants and in-process impurities, in order to achieve a tighter binding of the rAAV vector to anionic exchangers. Iodixinol step gradients are not readily scalable to commercial scale processes described herein.

The inventors of the present application have discovered that rAAV vector particles can be isolated from contaminants, such as production culture contaminants or in-process contaminants, by capture and elution from apatite resins. Thus, in addition to capturing product from a crude feedstream, the apatite column clears a variety of process-related impurities, including host cell and adenovirus proteins, glucans, and serum proteins, as well as providing additional clearance factors for helper virus (such as Ad5 helper virus).

Apatite resins are chromatography media comprising minerals of calcium phosphate, including without limitation ceramic hydroxyapatite (CHT) and ceramic fluoroapatite (CFT). Apatite chromatographic media are also referred to as mixed mode or multi-mode media because apatite has functional groups that provide more than one binding chemistry. Without wishing to be bound by theory, apatite media provide the opportunity for calcium metal affinity binding, hydrogen bonding, positive charge repulsion, positive charge attraction, negative charge repulsion, and negative charge attraction via a host of different chemical groups, including hydroxyl residues present on the backbone, positively charged calcium moieties and negatively charged phosphate moieties present on the resin. Each binding chemistry applies to mixed mode binding just as it does for single mode chromatography. However, unlike in single mode chromatography, the various binding and elution chemistries are not independent and can work in opposing ways. For example, increasing the ionic strength can drive hydrophobic binding. (T. Kawasaki, M. Niikura, and Y. Kobayashi, *J. Chrom.* 515:125-148 (1990) and P. S. Gagnon, P. Ng, J. Zhen, C. Aberin, and J. He, *BioProcess Int'l* 4:50-60 (2006)). Specifically, CHT and CFT are spherical, macroporous forms of hydroxyapatite $(Ca_5(PO_4)_3OH)_2$ sintered at high temperatures to convert the mineral from a crystalline to a ceramic form. This yields a chromatography medium with a macroporous structure providing a large surface area, limited mass-transfer resistance, high mechanical strength, and base resistance. Sintering at different temperatures and times results in different physical structures-types I and II-which are identical chemically but offer different capacities for different classes of molecules. CFT differs from CHT in that it is a composite of fluoroapatite and hydroxyapatite prepared by chemically replacing the hydroxyl groups with fluorine groups to increase stability to acidic conditions. CFT and CHT resins are commercially available (e.g., from Bio-Rad Laboratories, Inc.).

The inventors of the present invention have surprisingly discovered that the presence of polyethylene glycol (PEG) in the loading buffer dramatically increases the capacity and reproducibility (by reducing the variable breakthrough of rAAV particles in the flow-through) of rAAV vector particle binding to apatite resins. Without wishing to be bound by theory, one attribute of rAAV vectors which distinguishes them from the majority of process-related impurities is the large physical size of the particles. This size differential was exploited in the capture and wash steps by including polyethylene glycol (PEG) in the chromatography binding and wash buffers to preferentially increase the partitioning coefficients of larger molecules to the bound state based on energetically favorable sharing of hydration shells. While use of PEG in purifying viral and bacteriophage vectors has been described in the art, unlike the present invention, it was used primarily as a precipitating agent to physically aggregate and remove viral particles from solution. Since PEG is known in the art to facilitate aggregation and precipitation of viral particles and rAAV has been described in the art to form aggregates at ionic strength below 200 mM (Wright et al., *Molecular Therapy* 12:171-178 (2005)), the effect of PEG on rAAV vector binding to apatite resins was unpredictable. PEG was known in the art to facilitate binding of immunoglobulin molecules to ion exchange resins as described, for example, in Gagnon, *J. Chromtogr.* 743A:51-55 (1996), and for charged hydrophobic mixed mode resins as described, for example, in Gagnon et al., $22^{nd}$ *International IBC Conference on Antibody Production and Development*, Mar. 4-6, 2009.

The inventors of the present application have determined based on experimentation with PEG6000 over a concentration range between 3-10% (w/v) in the feedstream that a relative concentration of about 5% (w/v) PEG6000 was optimal. One of ordinary skill in the art will appreciate that other species and molecular weights of PEG can be utilized including without limitation PEG8000, PEG10000, and PEG15000, and that the relative concentration of PEG at the final concentration in the rAAV vector solution can be empirically determined such that at the appropriate concentration of PEG, rAAV vector particles in the solution are driven to bind to the apatite resin but do not form aggregates or physically precipitate.

In some embodiments, the rAAV vector particles are isolated from production culture contaminants by capture on an apatite resin in the presence of PEG and elution of the bound rAAV particle from the apatite resin in a phosphate buffer. In preferred embodiments, the rAAV vector particles are isolated from production culture contaminants by capture on an apatite resin in the presence of PEG and elution of the bound rAAV particle from the apatite resin in a buffer in the absence of PEG. In some embodiments, rAAV particles comprising capsids that are weak anionic binders are isolated from production culture contaminants by capture on an apatite resin in the presence of PEG and the bound rAAV particle eluted of from the apatite resin in a buffer in the absence of PEG. In more preferred embodiments, rAAV particles comprising capsids of serotype 1 (rAAV-1 serotype) are isolated from production culture contaminants by capture on an apatite resin in the presence of PEG and the rAAV-1 serotype capsid containing particles bound to the resin are eluted in buffer in the absence of PEG. In some embodiments, the rAAV vectors particles are isolated from production culture contaminants according to a method comprising loading a feedstream in a loading buffer in the absence of phosphate but in the presence of PEG and eluting the bound rAAV from the apatite resin in an elution buffer comprising phosphate and lacking PEG.

While apatite chromatography in the presence of PEG represents an efficient capture or binding strategy for purification of rAAV vectors, many in-process impurities were also retained by the apatite resin at pH 7.0. Without wishing to be bound by theory, proteins present in the feedstream at basic pH (pH greater than 7.0) would be more likely to have a net negative charge and be repelled by the negative phosphate binding sites present on the apatite resin, thereby reducing the overall cation exchange binding capacity of the chromatographic resin. Given the mixed mode nature of apatite resins, however, binding via positive charge attraction and metal affinity could still occur.

Borate buffers are routinely used in the art as basic buffering systems because of their desirable manufacturing properties including without limitation ease of preparation, optimal solubility, excellent buffering capacity, and low cost. Therefore borate buffers as the model basic buffering system were evaluated for rAAV capture on apatite resins. One of ordinary skill in the art can appreciate that other basic buffers could be evaluated to determine if they reduced the level of in-process impurity binding to apatite resins in the presence of PEG. Other basic buffers may be tested and use for rAAV capture. In some embodiments, the apatite loading buffer in the absence of PEG comprises a borate buffer. In preferred embodiments, the borate buffer is formulated at a pH between about 8.0 to about pH 9.9. In a preferred embodiment, the borate buffer is formulated at a pH of about 9.0. In some embodiment, the borate buffer is at a concentration between about 5 mM to about 500 mM. In more preferred embodiments, the borate buffer is formulated at about 20 mM borate, pH 9.0. In some embodiments, the 20 mM borate buffer at pH 9.0 specifically reduces the capture of small molecule in-process impurities on the apatite resin.

In some embodiments, the feedstream is loaded onto the apatite resin in a buffer containing phosphate in the presence of PEG by online mixing of the feedstream with a phosphate buffer comprising PEG at twice the final concentration of PEG. In some embodiments, the pH of the phosphate buffer is between pH 6.5 and pH 7.0. In some embodiments, the PEG is PEG6000. In some embodiments, the concentration of PEG6000 in the loading buffer is between about 3% (w/v) and about 10% (w/v). In more preferred embodiments, the concentration of PEG6000 in the loading buffer is about 5% (w/v). In some embodiments, the concentration of phosphate in the loading buffer for the apatite resin is between 5 mM and 500 mM In some embodiments, the binding capacity of the apatite resin in the presence of PEG is enhanced relative to the binding capacity of the apatite resin in the absence of PEG. In some embodiments, the binding capacity of the apatite resin for rAAV vector particles in a feedstream in the presence of PEG is enhanced from about one-half of a log to about ten logs relative to the binding capacity of the apatite resin in the absence of PEG. In preferred embodiments, the binding capacity of the apatite resin for rAAV particles present in a feedstream in the presence of PEG is enhanced eight logs. In some embodiments, the binding capacity of the apatite resin for rAAV vector particles in a feedstream in the presence of PEG is at least about $10^6$ particles of rAAV per ml of resin to about $10^{16}$ particles per ml of resin (such as about any of $10^6$, $10^7$, $10^8$, $10^9$, $10^{10}$, $10^{11}$, $10^{12}$, $10^{13}$, $10^{14}$, $10^{15}$, $10^{16}$ particles per ml of resin). In some embodiments, the binding capacity of the apatite resin in the presence of PEG is about $10^1$ particles per ml of resin.

While this surprising binding capacity of approximately $10^{12}$-$10^{14}$ DRP of rAAV-1 per ml of apatite resin in the presence of PEG allows for highly efficient, cost-effective scaling of commercial rAAV-1 purification, one of ordinary skill in the art will appreciate that the binding capacity represents the maximum number or rAAV-1 that will bind per ml of resin and is not intended to operationally limit the scope of the invention. Indeed the inventors appreciate that rAAV-1 vector harvest cultures that contain less than $10^{14}$-$10^{16}$ DRP of rAAV-1/ml may be purified by the present invention.

In some embodiments, the rAAV particles bound to the apatite medium is washed before eluting the rAAV particles from the resin. In some embodiments, the apatite chromatography medium is washed one or more times with a wash buffer containing decreasing concentrations of PEG to remove the in-process impurities. In some embodiments, the apatite chromatography medium is washed one or more times with a wash buffer containing between about 3% (w/v) and about 10% (w/v) PEG. In some embodiments, the wash buffer contains about any of 10% (w/v), 9.5% (w/v), 9% (w/v), 8.5% (w/v), 8% (w/v), 7.5% (w/v), 7% (w/v), 6.5% (w/v), 6% (w/v), 5.5% (w/v), 5% (w/v), 4.5% (w/v), 4% (w/v), 3.5% (w/v), and 3% (w/v) PEG. In some embodiments, the apatite medium is washed with a wash buffer containing PEG at a concentration higher than the PEG concentration used for allowing binding of the rAAV particles to the apatite medium. In some embodiments, the apatite medium is further washed with decreasing concentration of PEG. In some embodiments, the wash buffer contains buffers known in the art. In some embodiment, the wash buffer comprises a buffer selected from the group consisting of borate, N-2-Hydroxyethylpiperazine-N'-2-ethanesulfonic acid (HEPES), and Tris-HCl. In some embodiments, the wash buffer is at basic pH. In some embodiments, the wash buffer has a pH between pH 7.0 and pH 10.0, between pH 7.2 and pH 10.0, between pH 7.4 and pH 10.0, between pH 7.6 and pH 10.0, between pH 7.8 and pH 10.0, pH 8.0 and pH 10.0, pH 8.2 and pH 10.0, between pH 8.4 and pH 10.0, between pH 8.6 and pH 10.0, between pH 8.8 and pH 10.0, between pH 9.0 and pH 10.0, between pH 9.2 and pH 10.0, between pH 9.4 and pH 10.0, between pH 9.6 and pH 10.0, or between pH 9.8 and pH 10.0. In some embodiments, the wash buffer has a pH at 7.0, 7.2, 7.4, 7.6, 7.8, 8.0, 8.2, 8.4, 8.6, 8.8, 9.0, 9.2, 9.4, 9.6, 9.8, or 10.0. In some embodiments, the wash buffer further comprises between 100 and 500 mM phosphate. In some embodiments, the wash buffer further comprises between 50 and 250 mM NaCl.

In some embodiments, the rAAV vectors isolated from a feedstream by capture on an apatite resin in the presence of PEG are eluted in a buffer in low concentrations of PEG. In some embodiments, low concentrations of PEG are between about 2.9% (w/v) and about 0.1% (w/v) PEG. In some embodiments, the rAAV vectors isolated from a feedstream by capture on an apatite resin in the presence of PEG are eluted in a buffer in the absence of PEG. In preferred embodiments, the rAAV vectors isolated from a feedstream by capture on an apatite resin in the presence of PEG are eluted in a buffer containing phosphate in the absence of PEG.

In some embodiments, the rAAV vectors isolated from a feedstream by capture on an apatite resin in the presence of PEG are eluted in a buffer containing phosphate. In some embodiments, the rAAV vectors isolated from a feedstream by capture on an apatite resin in the presence of PEG are eluted in a buffer containing phosphate at a concentration between about 0.1 mM to about 500 mM (such as, between about 1 mM to about 250 mM, between about 10 mM to about 100 mM). In preferred embodiments, the rAAV vectors isolated from a feedstream by capture on an apatite resin in the presence of PEG are eluted in a 50 mM phosphate buffer.

The inventors of the present application have discovered that rAAV vectors present in a feedstream can be isolated by capture on an apatite resin in the presence of PEG. However if helper viruses used in the production culture (such as adenovirus) are present in the feedstream applied to the apatite resin, they are captured by the apatite resin in the presence of PEG. rAAV vector particles captured by the apatite resin in the presence of PEG can be easily isolated from adenovirus by their elution profile in phosphate buffers. rAAV vector particles bound to the apatite resin in the presence of PEG, elute, in the absence of PEG, in buffers containing as low as 0 mM phosphate; whereas helper virus adenoviral particles are retained on the apatite resins under concentrations of phosphate used to elute the rAAV vector particles. Experimentally, rAAV vectors were found to elute in a single sharp peak in as little as 50 mM phosphate in the absence of PEG, whereas helper virus such as adenovirus if present were retained on the resin. In spike-in studies in which rAAV feedstreams were spiked with 89 DNase-resistant particles (DRPs) of infectious adenovirus and subjected to chromatography on apatite resins in the presence of PEG, the rAAV vectors were captured on the apatite resin and eluted in 50 mM phosphate buffer in the absence of PEG, while approximately 4 logs of adenoviral proteins were retained on the apatite resin. Accordingly, in some embodiments, the rAAV vectors present in a feedstream are isolated from contaminating helper virus by capture on an apatite resin in the presence of PEG and elution in phosphate buffers in the absence of PEG. In some embodiments, the phosphate buffers are formulated at concentrations that retain contaminating helper virus bound to the apatite resin. In some embodiments, two to eight logs of adenovirus are retained per ml of apatite resin. In some embodiments, the rAAV vectors present in a feedstream are isolated by elution from an apatite resin in 0-500 mM phosphate buffer (such as 0-400 mM, 0-300 mM, 0-200 mM, 0-100 mM, 0-50 mM) under conditions which retain helper virus bound to the apatite resin.

Production systems known in the art to produce rAAV vectors may include production media containing serum in the range of 0.5/6-20% (v/v), or may be devoid of serum altogether. Furthermore, purification schemes described in the art may include one or more concentrations steps that may result in an increase of serum proteins and other serum components in the feedstream applied to the apatite resin. For example, the production culture supernatant as described herein which was formulated with 1% (v/v) serum was concentrated approximately twenty-fold in the TFF step, such that the feedstream loaded onto the apatite resin contained as much as 20% serum protein contaminants compared to a feedstream concentrate from a production culture formulated without serum. The inventors of the present application tested the apatite capture methods provided herein with feedstream concentrates from production cultures formulated in the presence or absence of serum. The presence of serum proteins in the feedstream was found to have no effect on the performance of the apatite chromatography step.

Heat Inactivation of Helper Virus (Heat Kill)

If infectious adenovirus is used as a source of helper virus in the production cultures for rAAV production, an optional heat inactivation (heat kill) step can be incorporated to inactivate any residual adenoviral particles which may be present in the feedstream. The heat kill step takes advantage of one of the major differences between AAV and adenovirus: adenovirus particles are inactivated at temperatures of approximately 54-56° C., while AAV and rAAV viral particles are stable and unaffected by those temperatures. In the present invention, the inventors have adjusted the heat inactivation step to accommodate larger scale process optimization such as the 250 L scale production cultures performed herein. In particular, the apatite eluate was heat-inactivated in a sterile, single use 5 L bioprocessing bag on a temperature-controlled rocking platform set to 53° C. at a rocking speed of 40 RPM, with a 12° angle for mixing (20 L Wave heater pan). The apatite eluate was incubated on the platform until it reached 52° C., and then held at that temperature for an additional 10 minutes. $MgCl_2$ was added to the apatite eluate at a final concentration of 2 mM to stabilize the rAAV vector during heating. One of ordinary skill in the art can appreciate that the scale, final set point for heating, and heating time can be empirically tested to find optimal conditions to inactivate adenoviral particles while maintaining the infectivity and integrity of the rAAV particles. The heat inactivation step can be omitted for purification of rAAV particles from production cultures that utilize plasmid constructs to provide helper function.

Hydrophobic Interaction Chromatography

Hydrophobic interaction chromatography (HIC) is a technique for separating biomolecules based on differences in their surface hydrophobicity. Thus, HIC is considered an orthogonal method to the other purification steps in the AAV process. HIC chromatographic media contain hydrophobic ligands such as linear chain hydrocarbons (e.g., propyl (C3), butyl (C4), hexyl (C6), or octyl (C8)) or aromatics (e.g., phenyl). In pure water, the hydrophobic effect is too weak for functional interaction between the ligand and proteins, or between the proteins themselves. However, lyotropic salts enhance hydrophobic interactions, and the addition of salt drives the capture of proteins to HIC media. For this reason, HIC resins are usually loaded under high salt concentrations and eluted at lower salt concentrations. As one of ordinary skill in the art will appreciate, ammonium sulfate [$(NH_4)_2SO_4$] is the most commonly used salt to control capture of proteins via HIC chromatography, because of the high lyotropic ranking of both ammonium and sulfate ions in the Hofmeister series, and the high solubility of the salt. In the present invention, rAAV particles present in a feedstream were loaded onto a HIC resin by in-line mixing of a 75:25 (volume:volume) ratio of 2 M ammonium sulfate+50 mM BisTris buffer (pH 7.0):feedstream, respectively. In-line mixing of the feedstream with the loading buffer avoids the risk of any rAAV vector precipitation by the high concentration of ammonium sulfate present in the buffer. As one of ordinary skill in the art can appreciate the concentration of salt (ammonium sulfate) can be manipulated to achieve the optimal concentration for rAAV binding. Accordingly, in some embodiments, the ammonium sulfate concentration is between 1 M and 3 M. In some preferred embodiments, the ammonium sulfate concentration in the loading buffer is 2 mM. As one of ordinary skill in the art can appreciate, in-line mixing of the ammonium sulfate and feedstream is performed for convenience and flow of the unit operation, but one could easily mix the feedstream with the appropriate concentration of loading buffer by any means known in the art and then load feedstream+loading buffer solution onto the HIC chromatographic media.

Co-solvents can also affect the hydrophobic interaction. For example, ethylene or propylene glycol can reduce the interaction between protein and the immobilized ligand and thus be useful for improving elution profiles. Accordingly, the HIC column was washed with a 75:25 (v:v) mixture of 2M ammonium sulfate+50 mM BisTris buffer (pH 7.0):50 mM BisTris (pH 7.0)+10% Propylene Glycol (v:v) buffer (EMD BioSciences), and rAAV was eluted in a low salt buffer plus propylene glycol (800 mM ammonium sulfate+50 mM BisTris buffer (pH 7.0)+4% Propylene Glycol. Under those elution conditions, any residual helper virus and proteins present in the feedstream loaded onto the column would remain bound to the column. The Propylene Glycol in this example was added to the buffers to sharpen the elution profile, in comparison to the broad elution profile of the buffer without Propylene Glycol, but is optional in the process.

Examples of suitable hydrophobic resins include without limitation Tosoh Butyl 650M, Tosoh SuperButyl 650C, Tosoh Phenyl 650C, and EMD Fractogel Phenyl (Tosoh Bioscience LLC, PA)

Waste from rAAV production processes requires stringent decontamination before disposal for at least two reasons: (1) the product comprises a viral vector; and (2) production cultures commonly use live adenovirus type 5 (Ad5) as a helper virus for rAAV production. Liquid waste from chromatography operations is typically decontaminated first with bleach at point of use and then undergoes further decontamination by holding at high pH before neutralization and disposal.

The ammonium sulfate present in the HIC buffers reacts with both bleach and sodium hydroxide to release hazardous chlorine and ammonia gas respectively. Therefore, a primary consideration for process optimization of the HIC chromatography step was the development of a suitable buffer system that could be safely decontaminated by methods known in the art.

As one of ordinary skill in the art can appreciate, buffers with high salt concentrations used in hydrophobic interaction chromatography must be further screened for viscosity issues which can result in high backpressures that can either limit flow rates or cause mixing problems, thereby increasing the risk of precipitation of the product by salt crystallization in the buffers occurring at temperatures used for storage or operation. Based on the data in Table 6 below and consideration of the factors described above, the inventors selected 1 M sodium citrate (pH 7.0) as the optimal buffer for binding of rAAV vectors to the HIC chromatographic media, although citrate buffers can be used in hydrophobic interaction chromatography at concentrations ranging from 0.5 M to 2.0 M.

Buffer Exchange by Size Exclusion Chromatography (SEC)

Numerous methods are known in the art to perform the buffer exchange described herein, including TFF and dialysis. Use of size exclusion chromatography has the additional advantage of providing further protein clearance of proteins sized to pass through the pores in the resins and being relatively fast in terms of time necessary to exchange the buffers. Buffer exchange was performed at this step to ensure that the HIC eluate of the previous step was exchanged to an appropriate buffer for rAAV binding to the final anion exchange chromatography step in the process.

Adventitious Agent (Viral Clearance)

Optionally, a further step to clear trace contaminants, such as adventitious viruses which may be present in the feedstream, can be incorporated into the process, thereby yielding a commercially reasonable orthogonal process. Thus, in some embodiments, the process further includes a viral clearance filter. Examples of such filters are known in the art and include Millipore Viresolve NFR (50 nm), Pall Ultipore VF (50 nm), and Asahi 70 nm.

Anionic Exchange Chromatography

An anion exchange capture step for the rAAV vector subjected to apatite chromatography was performed as a final concentration and polish step. Suitable anion exchange chromatography media are known in the art and include without limitation, Unosphere Q (Biorad, Hercules, California), and N-charged amino or imino resins such as e.g., POROS 50 PI, or any DEAE, TMAE, tertiary or quaternary amine, or PEI-based resins known in the art (U.S. Pat. No. 6,989,264; N. Brument et al., *Mol. Therapy* 6(5):678-686 (2002); G. Gao et al., *Hum. Gene Therapy* 11:2079-2091 (2000)). One of ordinary skill in the art can appreciate that wash buffers of suitable ionic strength can be identified such that the rAAV remains bound to the resin while other in-process impurities including without limitation glucans which may be introduced by leaching from various filters utilized in the purification steps are stripped away. In some embodiments, the wash buffer is 60 mM NaCl and the rAAV vector is eluted from the column with 130 mM NaCl, such that any residual trace in-process impurities present, such as serum albumin or helper virus, are retained on the column.

EXAMPLES

Example 1: Harvesting rAAV-1 from Culture Medium-Clarification & Benzonase® Digestion Spent rAAV-1 production medium (supernatant) from a 250 L rAAV-1 viral production culture produced by any method known in the art containing the rAAV-1 vector was clarified to remove any cells contained in the supernatant. The supernatant was passed through a series of filters connected in series, including: (1) a Millipore Millistak+0 HC Pod Filter, Grade D0HC (Millipore Corp., Bedford, MA) (4 times); (2) a Millipore Millistak+m HC Pod Filter, Grade A1HC; and (3) an Opticap® XL10 Millipore Express SHC Hydrophilic Membrane 0.2 μm Filter at a rate of 5 liters per minute (LPM) which was reduced stepwise to 4 LPM.

All filters were prewashed in reverse osmosis/de-ionized ("RO/DI") water per manufacturer's specifications. The flow-through was collected into a bioprocess bag for Benzonase® digestion. A final concentration of 2 units/ml of Benzonase® (EM Industries catalog number 1.01695.0002) was dissolved in the rAAV-1 production medium and added to the clarified viral supernatant to achieve a final concentration of 2.5 units/ml. The supernatant plus Benzonase® was incubated at ambient temperature with constant recirculation at 4 LPM to allow for DNA digestion. Data from the Benzonase® digestion is shown in FIG. 1, which demonstrates that no high molecular weight DNA was present following Benzonase® digestion.

Example 2: Removal of Production Contaminants Via Anionic Exchange

The rAAV-1 clarified and Benzonase®-digested supernatant from Example 1 was passed over a series of two-inch by twenty-two-inch Pall Mustang® Q ("MQ") filters connected in series (Pall Corp., catalog number NP6MSTGQP1). Prior to loading of the rAAV-1 viral, supernatant the filters were sanitized with 15 L of 0.5 M NaOH at 0.5 LPM with a holding time of 15 minutes, charged by rinsing with 15 L TMEG+2M NaCl (TMEG: 0.05 M Tris-HCl, pH 7.5, 1 mM 2-mercaptoethanol, 1 mM $Na_2EDTA$, 10% (v/v) glycerol) at a rate of 6 LPM, and equilibrated with 15 L of vector production medium at 6 LPM. The supernatant was then pumped at a rate of approximately 6 LPM through the series of filters and collected into a bioprocessing bag. At the ionic strength of the production medium, the anionic exchange MQ filter was demonstrated to clear helper virus and residual DNA, among other impurities, from the rAAV-1 supernatant by binding of the contaminants to the charged membrane. At the ionic strength of the production culture, however, the rAAV-1 vector present in the supernatant flowed through the anionic exchange membrane. During process optimization it was determined experimentally that using a single MQ filter resulted in a breakthrough of contaminants in the process, including the Ad5 helper virus. Consequently a second filter was added in series or in tandem in the process.

Example 3: Concentration of rAAV-1 Vector Supernatant

The complete rAAV-1 vector production supernatant processed in Examples 1 and 2 was concentrated approximately 20-fold via tangential flow filtration ("TFF") from an initial volume of approximately 250 L to a volume of approximately 12.5 L. Tangential flow polyethersulphone filter cartridges with a 100 kD molecular weight cut off, C screen and a 5 $m^2$ total surface area (Millipore Pellicon® 2 Biomax, Catalog No. P2B100C05) were flushed with 50 L of RO/DI water, sanitized with 15 L of 0.5 M NaOH with a 15 minute hold step, flushed again with 100 L of WIFI (HyPure™ WFI purified water; HyClone, Logan, UT), flushed with 15 L TMEG+2M NaCl, and finally equilibrated with 15 L of rAAV-1 production medium. The supernatant was passed through the TFF cartridge at a flow rate of approximately 3 LPM with a recirculation rate of 16 LPM. The TFF material retained on the filter ("retentate") was concentrated to approximately 10.5 L and was transferred to a reservoir. The filter was flushed with approximately 2 L of production medium. The wash and concentrate were then pooled to yield a final volume of approximately 12.5 L.

Concentration of rAAV-1 to a volume of 12.5 L by TFF also concentrated the remaining rAAV-1 production contaminants in the solution by approximately 20-fold. Thus, a manufacturing hold step was introduced following the TFF step, during which the TFF concentrate was filtered though a 4-inch Opticap 0.22 μM filter membrane (Millipore Opticap® Catalog No. KVSC04HB3). This extra filtration step enables the rAAV-1-containing TFF concentrate to proceed to the next step in the process without requiring diafiltration and buffer exchange. The post-TFF material may be stored at 2-8° C. for any period of time, including as little as 24 hours to as much as 3 months or more, before further processing with no loss in stability as measured by vector yield or infectivity assessed by assays known in the art. Alternatively, TFF performed as described herein could be used at any step in the purification process to concentrate or buffer exchange the rAAV-1 vector.

Example 4: Resin Screening for rAAV-1 Vector Versus Process Impurity Binding Commercial FDA-approved processes for purification of proteins and other biologic products relies upon commercial-scale incorporating orthogonal processes. Orthogonal processes are processes which have more than one step or process for removal of in-process impurities, including both capture and flow-through steps for the final product such as, for example, an rAAV-1 vector. rAAV vectors (specifically rAAV-2) have been demonstrated in the art to bind anionic resins. rAAV vectors such as rAAV-1, -5, and -8 have been demonstrated to bind much less tightly than rAAV-2 to anionic exchangers in the presence of production components such as serum albumin, helper virus components, production media components and host cell DNA resulting in a less efficient and lower quality purification scheme.

Previous purification strategies described in the art for lower affinity anionic binders such as AAV-1 include an iodixinol step gradient which reduces the relative concentration of the production components in order to achieve a tighter binding of the rAAV vector to anionic exchangers. Iodixinol step gradients are not readily scalable to commercial scale processes such as those described herein. Therefore, in order to optimize rAAV vector purification for low affinity anionic binders such as rAAV-1 without the need to perform ultracentrifugation and step gradients, a number of resins were screened for their ability to bind rAAV vectors or exclude the rAAV vectors in the flow-through as compared to the ability to bind or flow-through commonly observed process impurities including host cell DNA, helper virus, serum albumin, serum proteins (if serum is included the production medium), and other low molecular weight proteins found in the production cultures in order to develop a commercially scalable, orthogonal, and efficient rAAV purification process.

Resin screening was performed using a 1 ml (5 cm bed height) column with linear flow rates recommended by the vendor for each resin at severely underloaded capacities relative to the manufacturer's recommendations. Spectrophotometric tracings of ultraviolet absorbance at 280 nanometers ($A_{280}$) were collected for binding to and elution from each resin. Peaks were analyzed by the appropriate assay for both rAAV-1 vector and representative process impurities. The data presented in FIG. 2 represents a typical spectrophotometric tracing for a typical resin in the list. Table 2 lists some of the resins screened as well as the relative binding affinities of the resin for the rAAV-1 vector and various process impurities.

TABLE 2

Screening of resins for binding of rAAV-1 compared to binding of process contaminants

| Resin | Resin Type | rAAV-1 | Helper Virus | Host Cell DNA | Serum Albumin | Serum Proteins |
|---|---|---|---|---|---|---|
| UnoS pH 5.5 | Cation Exchange | + | 0 | − | + | + |
| UnoS pH 7.0 | Cation Exchange | − | − | − | − | − |
| UnoQ pH 8.5 | Anion Exchange | + | ++ | ++++ | ++ | ++ |
| UnoQ pH 7.0 | Anion Exchange | + | +++ | ++++ | ++ | ++ |
| Fractogel EMD $SO_3$ | Cation Exchange | + | ++ | − | 0 | 0 |
| CHT | Apatite | + | 0 | ++ | + | + |
| CFT | Apatite | + | 0 | ++ | + | + |

TABLE 2-continued

| Screening of resins for binding of rAAV-1 compared to binding of process contaminants | | | | | | |
|---|---|---|---|---|---|---|
| Resin | Resin Type | rAAV-1 | Helper Virus | Host Cell DNA | Serum Albumin | Serum Proteins |
| HIC Phenyl | Hydrophobic Exchange | – | – | – | 0 | 0 |
| HIC Butyl | Hydrophobic Exchange | + | ++ | – | 0 | 0 |
| HIC Hexyl | Hydrophobic Exchange | + | ++ | – | 0 | 0 |
| HIC PPG | Hydrophobic Exchange | – | – | – | 0 | 0 |
| Source S | Ion Exchange | + | 0 | 0 | ++ | 0 |
| Source Q | Ion Exchange | + | 0 | 0 | ++ | 0 |
| TMAE | Ion Exchange | + | 0 | 0 | ++ | 0 |
| IMAC $FeCl_3$ | | 0 | 0 | – | + | + |
| Superdex 200 | Gel Filtration | void | void | chase | chase | chase |
| HW55 | Gel Filtration | void | void | chase | chase | chase |
| HW65 | Gel Filtration | void | void | chase | chase | chase |
| HW75 | Gel Filtration | void | void | chase | chase | chase |

Key: (–) = present in flow-through (no binding); + = weakly bound (eluted very early in the gradient); ++ to ++++ = stronger binding (eluted further along the gradient).

Example 5: Development of Apatite Chromatography in the Presence of Polyethylene Glycol ("PEG") for Capture of rAAV-1

Based on the results of the resin screening performed in Example 4, an apatite resin or ceramic apatite resin was chosen as one of the capture resins for rAAV-1. Initial experiments were performed using CFT II resins, but for later purification the resin was changed to CHT I, as discussed in detail below. Data indicated that both chromatographic resins performed equivalently. Experiments were performed to further increase the rAAV-1 binding capacity of the apatite resin and improve the ability of the resin to discriminate between rAAV-1 particles and other in-process impurities. Two key improvements to the function of the apatite resins were further developed as described herein: 1) the addition of PEG; and 2) development of the loading buffer conditions.

Based on the variable breakthrough of the apatite column due to capacity issues at commercially reasonable column sizes, PEG was mixed with the TFF concentrate (see Example 3 above) before loading on the apatite resin in order to increase binding of the rAAV-1 vector relative to other in-process impurities such as serum albumin, helper virus and other protein impurities which out-competed the rAAV-1 vector for binding to the column in Example 4.

Apatite chromatography in the presence of PEG represents an efficient capture or binding strategy for purification of rAAV-1 vectors, although many in-process impurities were also retained by the apatite resin at pH 7.0.

Experiments were performed to determine if modifying the buffering conditions could improve the resolution of rAAV-1 from other in-process impurities. Small scale experiments were performed using an AKTAexplorer FPLC System (GE Healthcare, Piscataway, NJ) equipped with 1.2 mL Tricorn 5 columns (GE Healthcare) packed at a 6 cm bed height with CFT resin, run at a flow rate of 150 cm/hr. Those columns were evaluated for rAAV-1 vector capture versus binding of bovine serum albumen ("BSA"), a model small molecule in-process impurity, in various buffer systems in the presence or absence of 5% PEG6000.

rAAV-1 or BSA was injected in small volumes (<5% of total volume) on the CFT column in the buffer system to be tested, either in the presence or absence of 5% (w/v) PEG6000. Small volumes were used in order to obviate the need for buffer exchange of the samples. Products were eluted along a 500 mM $PO_4$ gradient. 50 mM 2-(N-morpholino) ethanesulfonic acid ("MES") was used to buffer the system at pH=6.50, and 20 mM borate was used to buffer the system at pH 9.0.

The data presented in Table 3 demonstrate that rAAV-1 vector binding to the apatite resin was essentially the same at pH 6.5 or pH 9.0 in the presence of 5% (w/v) PEG6000, while binding of BSA, the model small molecule in-process impurity, was dramatically reduced at pH 9.0 in the presence or absence of 5% (w/v) PEG6000, as indicated by the spectrophotometric tracings (data not shown). Further analysis of the reduced capacity of BSA to bind to the apatite column at basic buffer loading conditions (i.e., pH=9.0) by enzyme-linked immunosorbent assay ("ELISA") demonstrated that most BSA (~78%) was present in the flow-through at pH 9.0 buffer conditions, while additional levels of clearance or reduction in BSA binding could be achieved during subsequent wash steps (~19%), leaving only ~0.1% of the BSA loaded onto the column actually bound to the apatite resin and co-eluting with the rAAV-1 vector. rAAV-1 particles were stable at pH=9.0, as indicated by no loss of infectivity or decrease in the number of DNase-resistant particles ("DRP") eluted.

TABLE 3

| Relative strength of binding of rAAV-1 and BSA to apatite resin at pH = 6.5 or pH = 9.0, with or without 5% (w/v) PEG6000 | | |
|---|---|---|
| Binding conditions | BSA | 5% (w/v) PEG6000 |
| pH = 6.50 | ++ | + |
| pH = 6.50 + 5% (w/v) PEG6000 | ++ | ++++ |
| pH = 9.0 | + | + |
| pH = 9.00 + 5% (w/v) PEG6000 | + | ++++ |

Key: + = weak binding;
++ = medium binding;
++++ = strong binding.

Example 6: Effect of Serum in the rAAV-1 Harvest Culture on rAAV-1 Capture Via Apatite Chromatography in the Presence of PEG rAAV-1 vector production cultures or rAAV-1-containing feedstreams to be purified by the methods described herein may contain serum and serum proteins if the production cultures were grown in medium containing serum. While rAAV-1 vector production that uses very low concentrations of serum (i.e., 1% or less)(see, e.g., U.S. Pat. No. 6,995,006) has been described, concentration of the production culture or feedstream as described in Example 3 can produce a feedstream that effectively contains 20% serum and serum proteins as a result of the 20-fold concentration of the production culture harvest. In order to evaluate the effect of serum components on performance of the apatite chromatography, experiments were performed on production cultures produced in the presence or absence of serum, in the presence or absence of PEG6000.

Two model rAAV-1 production cultures were used to assess capacity of the apatite resin (CFT type I) by traditional breakthrough analysis in a total of four column loading experiments. In one experiment, the production cultures contained serum; and in the second experiment, the production culture did not contain serum. Both feedstreams were tested in the presence of 5% (w/v) PEG6000 or in the absence of PEG. Feedstreams were representative of the harvest process, and were clarified culture supernatants that had been passed over an anion-exchange filter and concentrated 20-fold by tangential flow filtration as described herein. CFT type I columns were loaded by 1:1 online mixing of the feedstream with a borate buffer at pH=9.0. The buffer contained either 0% or 10% (w/v) PEG6000 (to achieve a final concentration of 5% (w/v) PEG6000). As columns were loaded, the flow-through was collected in a series of fractions which were analyzed for product by DRP-PCR. Functional capacity was defined as the point at which the product concentration at the outflow of the column just reached 1% of the concentration entering the column, after accounting for the online dilution. For column loads containing PEG, the remainder of the chromatography process was then run to assess vector recovery in the elution fractions.

Figure 3:
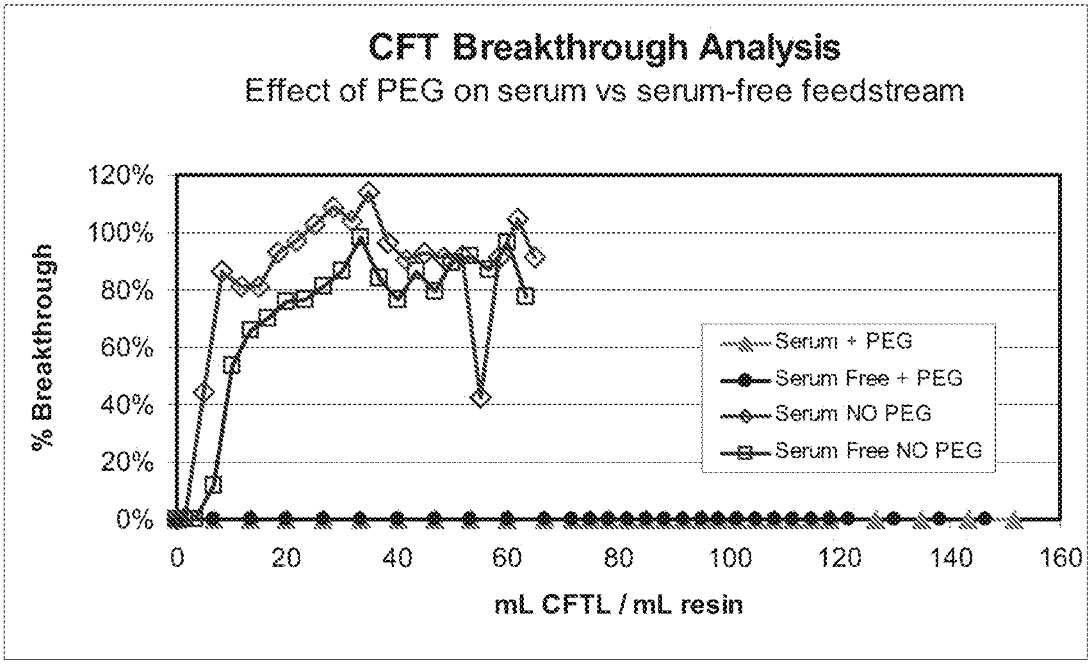
FIG. 3 presents a breakthrough capacity analysis with and without PEG. Two model rAAV production cultures were used to assess capacity of the apatite resin (CFT type I). Top panel: Breakthrough during load of serum-containing or serum-free feedstreams in the presence or absence of about 5% (w/v) PEG6000 in the load. Load volumes refer to the starting feedstream, before the 1:1 online dilution, and were normalized per mL resin volume. Bottom panel: Load volumes (ml) at which 1% breakthrough was observed, and recovery in elution fraction. The TFF harvests utilized in the experiment were at a concentration of approximately $10^{16}$ DRP/ml for the rAAV vectors. In the presence of about 5% (w/v) PEG6000, 150 mL of the TFF harvest was loaded onto the 1.2 mL CFT resin without breakthrough, which was defined as the presence of >1% rAAV in the column flow-through, corresponding to a load of $1.8\times10^{14}$ total rAAV DRP.

The data presented in FIG. 3 demonstrates that the addition of PEG6000 increases the capacity of the apatite resin for rAAV-1 vector binding regardless of whether serum was present in the production culture. Without wishing to be bound by theory, The post-TFF supernatant in the presence of PEG preferentially binds rAAV-1 to the apatite resin over other in-process impurities via an anionic interaction to the phosphate moieties which can be outcompeted by the presence of phosphate in the elution buffer. In addition, rAAV-1 binding to the apatite resin is further discriminated from in-process impurities via the metal interaction which can be outcompeted by the presence of salt. The binding of rAAV-1 to the phosphate moieties is not driven primarily by hydrophobicity, as the capture and elution buffers are formulated to be primarily ionic in nature (i.e., the elution buffer contains 50 mM phosphate, compared to elution buffers containing 150 mM phosphate or higher commonly used in eluting compositions bound by primarily hydrophobic interactions). Under these high salt, low phosphate elution conditions, residual helper virus, host cell DNA, and other low molecular weight proteins contained in the supernatant of the production cultures would, if present, be retained on the resin. Surprisingly, the data demonstrates that in the presence of PEG6000, rAAV-1 vectors produced in either serum-containing or serum-free media demonstrate a binding capacity for the apatite resins of at least $1.2\times10^{12}$ DRP/mL (a 1 mL load) to greater than $1.5\times10^{14}$ DRP/mL of resin (150 mL). In the absence of 5% (w/v) PEG6000, the binding capacity of the apatite resin for the TFF harvest was less than $2.4\times10^{12}$ DRP/mL for vectors produced in serum containing media and $7.2\times10^{12}$ DRP/ml for vectors produced in serum-free media, as no rAAV-1 vector was recovered in the CFT eluate.

Example 7: Purification of rAAV-1 Via Apatite Chromatography

The CHT Type I column was packed with 2 M NaCl and sanitized with 1 M NaOH. Before loading, the column was equilibrated with 6 column volumes ("CV") of 20 mM borate (pH=9)+5% (w/v) PEG6000. The TFF feedstream concentrate was loaded via a 3 mm BioProcess Skid (GE Healthcare) onto a 923 ml (14 cm diameter×6 cm bed height) CHT column prepared as described previously at a flow rate of 96 cm/hr. The TFF feedstream concentrate was mixed in-line with an equal volume of a 40 mM borate (pH=9)+10% (w/v) PEG6000 buffer to yield a final concentration of 20 mM borate (pH=9)+5% (w/v) PEG6000.

A series of 4 sequential washes were performed to remove in-process impurities while retaining the rAAV-1 vector on the column. Wash 1 ("the chase") was performed by in-line mixing of 5 CV of a 50:50 (volume:volume) 20 mM borate (pH=9.0)+5% (w/v) PEG6000:40 mM borate (pH=9.0)+10% (w/v) PEG6000 to chase all loading lines with PEG6000. Further, this step was found to preferentially increase the binding affinity of the rAAV-1 vectors. Wash 2 was performed with 15 CV of 150 mM potassium phosphate+20 mM borate (pH=9)+5% (w/v) PEG6000 to remove the majority of the serum albumin and other low molecular weight protein in-process impurities while retaining rAAV-1 on the column. Wash 3 ("WII" in FIG. 5) was performed with 15 CV of 20 mM borate (pH=9)+5% (w/v) PEG6000 to remove any residual phosphate so that the rAAV-1 remained bound to the column once the PEG6000 was removed. Wash 4 ("WIII" in FIG. 5) was performed with 5 CV of 20 mM HEPES (pH=7.0)+150 mM NaCl buffer to remove the PEG6000 and to adjust the salt concentration, thereby allowing discrimination between rAAV-1 and any residual helper virus or other in-process impurities, such as protein contaminants, which may remain bound to the column.

Figure 4:
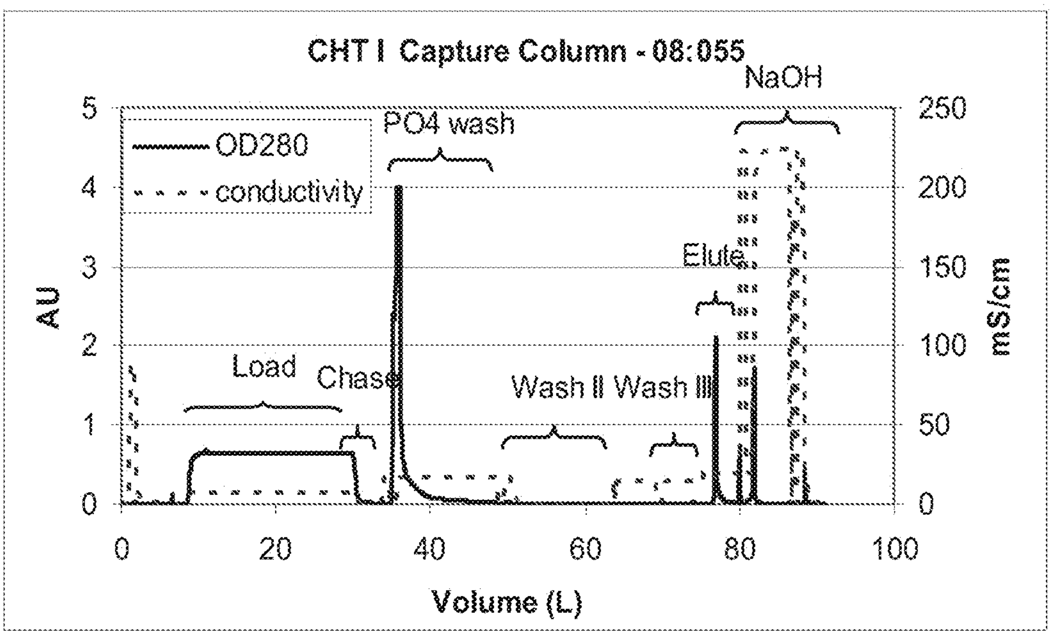
FIG. 4 presents a typical CHT I chromatogram. Shown are in-line, UV absorbance $A_{280}$ (AU, absorbance unit) and conductivity (mS/cm) measurements by the Amersham 3 mm Skid. Brackets mark the major segments of the program described in Example 7. "NaOH" marks the column decontamination step.
Figure 5:
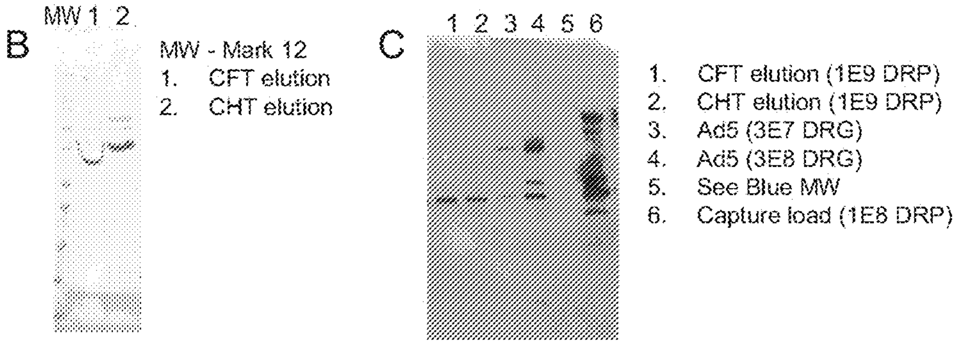
FIG. 5 shows the relative purity of rAAV vectors eluted from apatite resins. Panel A shows the distribution of vector between the flow-through/chase (FT), high phosphate/5% (w/v) PEG6000 wash ($PO_4$), the washes to remove phosphate and PEG6000 (WII/WIII), and the elution. None of the differences between the cases are significant within the precision of the analytics, and the lack of mass balance is typical. Panel B shows the relevant lanes from a Sypro orange-stained SDS PAGE with elution fractions from the apatite column. Each sample was loaded at $2\times10^{11}$ DRP/lane; the apparent migration difference between the lanes is a salt artifact due to having to concentrate the CFT elution by evaporation to a volume that would fit on the gel. The only predominant bands appear to be AAV capsid proteins. Panel C shows the relevant lanes of an Ad5 Western blot with lanes re-ordered for clarity, demonstrating comparable clearance of Ad5 proteins.

The rAAV-1 vector was eluted from the column by 6 CV of a 50 mM potassium phosphate+20 mM HEPES (pH=7.0)+150 mM NaCl buffer. FIG. 4 shows a typical spectrophotometric trace of UV absorbance at 280 nm ($A_{280}$) and conductivity for the CHT I chromatographic procedure. FIG. 5 shows the relative purity of rAAV vectors eluted from the apatite resin.

Glucan Clearance by Apatite Chromatography

Glucans are carbohydrates similar to cellulose which leach into the process from the cellulose-based depth filter used to harvest rAAV-1 particles from production cultures. Glucans at concentrations above ~1 ng/mL can interfere with standard *Limulus* amoebocyte lysate ("LAL") tests for bacterial endotoxin contamination. As demonstrated in Table 4 below, the apatite CHT Type I column cleared ~2.5 logs of glucans from the production culture. Under the buffer conditions described herein, the vast majority of the glucans were present in the flow-through and did not bind to the column.

TABLE 4

| Glucan clearance in the process | | |
|---|---|---|
| Processing step | Glucan concentration (ng/mL) | Total amount per lot (ng) (250 L scale) |
| Clarification | 10.4 | 2,600,000 |
| TFF | 136 | 1,541,016 |
| CHT elution | 1.9 | 4,769 |
| Post HIC and SEC | 0.2 | 662 |
| Final Anion Exchange Eluate | 0.1 | 71 |

Samples were assayed for glucan using an LAL-based kinetic chromogenic assay specific for glucans (Glucatell®, Cape Cod, MA).

Ad5 Helper Virus Clearance by Apatite Chromatography

To confirm that CHT chromatography cleared Ad5 from the feedstream, a preliminary spike-in study was performed using feedstream from the final upstream process. Ad5 spike levels were set based on data obtained from the phase I viral clearance study with CFT II resins, and three different load ratios of feedstream were used: 6.6 mL; 13.5 mL; and 33 mL of post-TFF feedstream per mL CHT resin.

The data presented in Table 5, Ad5 clearance by CHT was comparable to the 4 LRV clearance demonstrated approximately 4 logs of Ad5 viral clearance and appeared to be independent of volume of feedstream loaded, within the 5-fold range assessed. The low Ad5 recovery is consistent with previous data indicating that under the buffer conditions utilized the Ad5 binds tighter than rAAV-1 to the apatite resin.

TABLE 5

| Total infectious units of Ad5 in CHT column fractions | | | |
|---|---|---|---|
| | Fraction | | |
| Load ratio | 6.6 mL | 13.5 mL | 33 mL |
| Load | $9.0 \times 10^8$ | $1.3 \times 10^9$ | $9.0 \times 10^8$ |
| Flowthrough + chase | $<2.5 \times 10^5$ | $<3.6 \times 10^5$ | $<6.9 \times 10^5$ |
| $PO_4$ Wash | $2.9 \times 10^6$ | $2.7 \times 10^6$ | $<2.6 \times 10^6$ |
| Washes II & III | $3.6 \times 10^6$ | $2.2 \times 10^6$ | $2.8 \times 10^6$ |
| Elution | $<6.9 \times 10^4$ | $<6.9 \times 10^4$ | $<3.5 \times 10^5$ |
| Log reduction value (LRV) | >4.1 | >4.3 | >3.4 |

A total of $8\times10^9$ infectious particles of Ad5 (i.e., total particles with a P:I of ~10) were spiked into different volumes of post-TFF feedstream to run on 1.2 mL CHT columns. Columns were run at 100 cm/hr and fractions were collected to assay for vector by DRP and Ad5 by infectious titer assay. A spike-controlled version of the Ad5 infectivity assay was used since high concentrations of both the load and CHT elution samples are known to interfere in the cell-based assay. Ad5 clearance was determined as the Log Reduction Value ("LRV"), calculated as the logarithm of the total amount of Ad5 loaded divided by the total amount of Ad5 recovered in the elution fraction (Log Reduction Value).

Example 8: Heat Inactivation of Residual Helper Virus

A heat inactivation step was performed in order to inactivate and remove any residual helper virus present in the CHT I eluate. For smaller scale experiments, the CHT I eluate was divided between two 1 L PETG (Nalgene®) bottles and $MgCl_2$ added to a final concentration of 2 mM in order to increase the stability of the rAAV-1 vector. The bottles were incubated in a 53.5° C. water bath with mixing until the temperature in the bottle reached approximately 52° C. The bottles were then cooled by transfer to an ambient temperature water bath and mixed until the temperature in the bottle was no greater than 5° C. above ambient temperature. The heat-killed mixture was filtered through a 4-inch Opticap® 0.22 μM filter membrane (Millipore Opticap® catalog number KVSC04HB3). Alternatively, for larger scale experiments, the CHT I eluate was heat inactivated in a sterile, single use bioprocessing bag (Custom Hyclone 5 L bag, CX5-14 film) on a temperature controlled rocking platform with a temperature set-point of 53° C. at a rocking speed of 40 RPM and a mixing angle of 12° (20 L wave heater pan). The CHT I eluate was incubated on the platform until the temperature reached 52° C. and then held for an additional 10 minutes. To stabilize the rAAV-1 during heating, $MgCl_2$ was added to 2 mM final concentration. After heating, the product was filtered through a 0.2 μm filter and held overnight at ambient temperature to minimize possible temperature effects on the subsequent hydrophobic interaction column.

Example 9: rAAV-1 Capture via Hydrophobic Interaction Chromatography ("HIC")

HIC is a technique for separating biomolecules based on differences in their surface hydrophobicity. As such, HIC is considered an orthogonal method to the other purification steps in the rAAV-1 process. HIC media contain hydrophobic ligands such as linear chain hydrocarbons (e.g., propyl (C3), butyl (C4), hexyl (C6), or octyl (C8)) or aromatic hydrocarbons (e.g., phenyl). In pure water, the hydrophobic effect is too weak for functional interaction between the ligand and proteins, or between the proteins themselves. However, lyotropic salts enhance hydrophobic interactions, and adding such salts drives adsorption of proteins to HIC media. For this reason, HIC resins are usually loaded under high salt concentrations and eluted at lower salt concentrations.

HIC Chromatography with Ammonium Sulfate Buffers

Briefly, a 170 ml (6 cm diameter×6 cm bed height) HIC butyl column (Toyopearl® Butyl 650M; Tosoh Biosciences, Montgomeryville, PA; Catalog number 14702) was sanitized with several column volumes of 0.5 M NaOH and equilibrated with a 75:25 (volume:volume) mixture of 2 M ammonium sulfate+50 mM Bis Tris (pH=7.0):50 mM Bis Tris (pH=7.0). The heat killed rAAV-1 vector apatite eluate was loaded at a rate of 3.3 L/hr with in-line mixing at a 75:25 (volume:volume) ratio of 2 M ammonium sulfate+50 mM Bis Tris (pH=7.0):rAAV-1 apatite eluate. In-line mixing avoids the risk of any rAAV-1 vector precipitation by the ammonium sulfate present in the buffer. The column was washed with one or more column volumes of a 75:25 (volume:volume) of a 2 M ammonium sulfate+50 mM Bis Tris pH=7.0 buffer:50 mM Bis Tris pH=7.0+10% Propylene Glycol (volume:volume) (EMD Biosciences) buffer. The propylene glycol in this example was added to the buffers to sharpen the elution profile, compared to the broad elution profile of the buffer without propylene glycol, although it is optional in the process. The rAAV-1 vector was eluted from the column with 800 mM ammonium sulfate+50 mM Bis Tris (pH=7.0) buffer+4% propylene glycol. At the elution conditions utilized, any residual helper virus and proteins present in the load would remain bound to the column.

Waste from rAAV-1 production processes requires stringent decontamination before disposal, due to both the product being a viral vector and the use of live adenovirus type 5 (Ad5) as a helper virus for production. Liquid waste from chromatography operations is typically decontaminated first with bleach at point of use and then further decontaminated by holding at high pH before neutralization and disposal. Ammonium sulfate present in the HIC buffers reacts with both bleach and sodium hydroxide to release hazardous chlorine and ammonia gas respectively. Therefore, a primary consideration for process optimization of the HIC chromatography step was the development of a suitable buffer system that could be safely decontaminated by methods known in the art.

Screening for Suitable Buffers for rAAV-1 Binding to the HIC Column rAAV-1 vector was loaded onto columns in a variety of different buffer conditions and relative binding efficiency was determined by measuring the amount of rAAV-1 vector present in the flow-through fraction (Table 6). Buffers evaluated included both high concentration lyotropic salts traditionally utilized with HIC chromatographic processes and several low pH buffers where a mixed-mode interaction (HIC/cation exchange) could potentially occur. Both the Tosoh Butyl 650M and EMD Phenyl resins bound vector in several of the alternative buffers.

Buffers with high salt concentrations used in hydrophobic interaction chromatography must be further screened for viscosity issues which can result in high backpressures that can either limit flow rates or cause mixing problems and the risk of precipitation of the product due to salt crystallization at storage or operating temperatures of the buffers. Based on the data in Table 6 below, and after considering the factors described above, 1 M sodium citrate, pH=7.0 was chosen as the optimal buffer for binding of rAAV-1 vectors to the HIC chromatographic media.

TABLE 6

Screening for AAV1 binding in alternative buffers

| Buffer System Tested | Butyl 650M (% in flow-through) | EMD-Phenyl (% in flow-through) |
|---|---|---|
| 1.1M Sodium Sulfate (pH = 7) | 0% | 0% |
| 1M Sodium Citrate (pH = 7) | 0% | 0% |
| 1.3M Potassium Phosphate (pH = 7) | 3% | 3% |
| 2.9M NaCl, 50 mM Sodium Citrate (pH = 4) | 0% | 28% |
| 1M Glycine, 50 mM Sodium Citrate (pH = 4) | 4% | 1% |
| 50 mM Potassium Phosphate (pH = 4.5) | 3% | NT |
| 50 mM Sodium Citrate (pH 4) | 4% | NT |
| 2.9M NaCl, 50 mM Potassium Phosphate (pH 4.5) | 17% | NT |

Experiments were performed at ambient temperature on Tricorn 5/50 columns (6 cm bed height, 1.2 mL column volume) using purified rAAV-1 vector. Columns were equilibrated with the buffers listed and ~$2\times10^{11}$ DRP or rAAV-1 were loaded on the column. rAAV-1 was eluted over a 20 CV linear gradient from 145 mM Bis Tris (pH=7.0), 10% (v/v) propylene glycol. The flow-through was collected and assayed by DRP analysis for the fraction of rAAV-1 applied to the column that flowed through or did not bind.

Further characterization was performed on the clearance of in-process impurities on the HIC column in the various buffers demonstrating good binding of rAAV-1 in the previous experiment. The data in Table 7 below for model contaminant binding demonstrates that both adenovirus and DNA if present in the feedstream are effectively discriminated by the HIC chromatographic step.

TABLE 7

Relative binding of rAAV-1 versus model in-process impurities in different HIC buffers

| Buffer System | rAAV-1 | Ad5 | DNA |
|---|---|---|---|
| 0.1M sodium sulfate + bis tris buffer, pH = 7.0 | + | ++ | − |
| 0.8M sodium sulfate, bis tris buffer, pH = 7.0 | + | ++ | 0 |
| 1M sodium citrate, pH = 7.0 | + | ++ | 0 |
| 2.9M NaCl (50 mM sodium citrate to buffer at pH = 4.0) | − | − | 0 |

Key: "0" = no binding material present in flow-through;
"−" = very weak binder;
"+" = strong binder;
"++" = stronger binder.

Experiments were performed at ambient temperature on Tricorn 5/50 columns (6 cm bed height, 1.2 mL column volume). Columns were equilibrated with the buffers listed and the indicated samples were loaded on the column. Each sample was eluted over a 20 CV linear gradient. Samples were collected and assayed for the relevant load material.

HIC Chromatography with Sodium Citrate Buffers

The heat-killed rAAV-1 vector apatite eluate was subsequently loaded onto a HIC butyl column in order to further reduce any residual process impurities and as a concentration and desalting step. A 373 ml (6 cm diameter×8.9 cm bed height) HIC butyl column (Tosoh Biosciences Toyopearl® Butyl 650M catalog number 14702) was sanitized with several column volumes of 0.5 M NaOH and equilibrated with 5 CV of a 75:25 (volume:volume) mixture of 1 M Citrate+20 mM sodium phosphate:20 mM sodium phosphate. The heat-killed rAAV-1 vector CHT I eluate was loaded at a rate of 106 cm/hr with in-line mixing at a 75:25 (volume:volume) ratio of 1 M citrate+20 mM sodium phosphate:CHT I eluate. In-line mixing avoids the risk of any rAAV-1 vector precipitation. The column was washed with 5 CV of a 75:25 (volume:volume) mixture of 1 M citrate+20 mM sodium phosphate:20 mM sodium phosphate buffer. The rAAV-1 vector was eluted from the column with 6 CV of 0.35 M citrate+20 mM sodium phosphate. The column was then washed with 3.5 CV of 20 mM sodium phosphate buffer. This low salt wash (20 mM sodium) elutes a fraction of rAAV-1 vector particles that are hydrophobically distinct in their elution profile from the rAAV-1 vector particles that elute in the higher salt elution buffer. In fact, if the low salt eluted fraction was isolated and reapplied to the HIC column under the conditions described, that population of vector still eluted only in the low salt fraction, indicating that the fraction was not the result of a breakthrough in capacity of the column. Infectivity analysis suggests that this fraction of rAAV-1 likely represents a population comprising empty capsids, partially denatured capsids, less infectious capsid material, and partially full capsids. Therefore, this observation may lead to improvements in the separation of rAAV-1 particles that are less infectious and therefore less desirable as product material. At the elution conditions utilized any residual helper virus and proteins present in the load would remain bound to the column and thus should be present in the low salt strip.

Example 10: Buffer Exchange by Size Exclusion Chromatography ("SEC")

Buffer exchange by size exclusion chromatography provides additional protein clearance of proteins sized to pass through the pores in the resins, and is relatively fast in terms of time necessary to exchange the buffers. The buffer exchange performed at this step was to ensure that the HIC eluate of the previous step was exchanged to an appropriate buffer for rAAV-1 binding to the final anion exchange chromatography step in the process. A 3.2 L (14 cm diameter×21 cm bed height) Amersham Superdex® 200 prep grade resin (Amersham/GE Healthcare, Piscataway, NJ; Catalog number 17-1043-04) was packed and prepared by sanitizing with 2 M NaCl+1 M NaOH and equilibrated with 2.8 CV of 20 mM NaCl+20 mM Tris (pH=8.0). The HIC elution was sub-divided to process over the SEC in three sequential cycles of approximately 400 ml each, loading no more than 12.5% of the SEC column volume for each cycle. The product peaks (contained in the void volumes) from the three SEC cycles were collected in a single bioprocessing bag. The HIC eluate was loaded onto the column at a flow rate of 49 cm/hr. The column was chased and flushed with 1.4 CV of 20 mM NaCl+20 mM Tris (pH=8.0) and the rAAV-1 vector present in the HIC eluate was present in the void volume of the column. Following the collection of the void volume as described, the second and third fractions were loaded and collected on the same column sequentially as described previously for the first fraction.

Example 11: Adventitious Agent (Viral Clearance)

As an optional process to clear adventitious viruses which may be present as trace contaminants and thus yield a commercially reasonable orthogonal process, a viral clearance filter was introduced into the process. Examples of such filters are known in the art and include Millipore Viresolve® NFR (50 nm), Pall Ultipore® VF (50 nm), and Asahi 70 nm. A Millipore Viresolve® NFR (Millipore 4" Virosolve NFR filter Catalog number KZRV 04T C3) viral clearance filter was prepared according to manufacturers instructions, flushed with 20 mM NaCl+20 mM Tris (pH=8.0) and the SEC elution was filtered through the membrane. The filter was flushed with several volumes of 20 mM NaCl+20 mM Tris-HCl (pH 8.0) and pooled with the filtered SEC eluate.

Example 12: Anionic Exchange Chromatography

A second anion exchange capture step for the rAAV-1 vector was performed as a final concentration and polish step on a Unosphere® Q resin (Biorad, Hercules, CA). A 373 ml (8.9 cm diameter×6 cm bed height) column was sanitized with several column volumes of 0.5 M NaOH and equilibrated with 7 CV of 20 mM NaCl+20 mM Tris (pH=8.0) buffer. The SEC void volume fraction or optionally the viral filtered eluate was loaded at a rate of 309 cm/hr. The column was washed 10 CV of 60 mM NaCl. The ionic strength of the wash solution was chosen to retain rAAV-1 bound to the resin while stripping away any other in-process impurities, such as glucans which may be introduced by leaching from various filters utilized in the purification steps. The rAAV-1 vector was eluted from the column with 6 CV of a 130 mM NaCl. The ionic strength of the 130 mM NaCl salt elution will strip rAAV-1 from the column while any residual trace in-process impurities, such as serum albumin or helper virus would remain bound.

Figure 6:
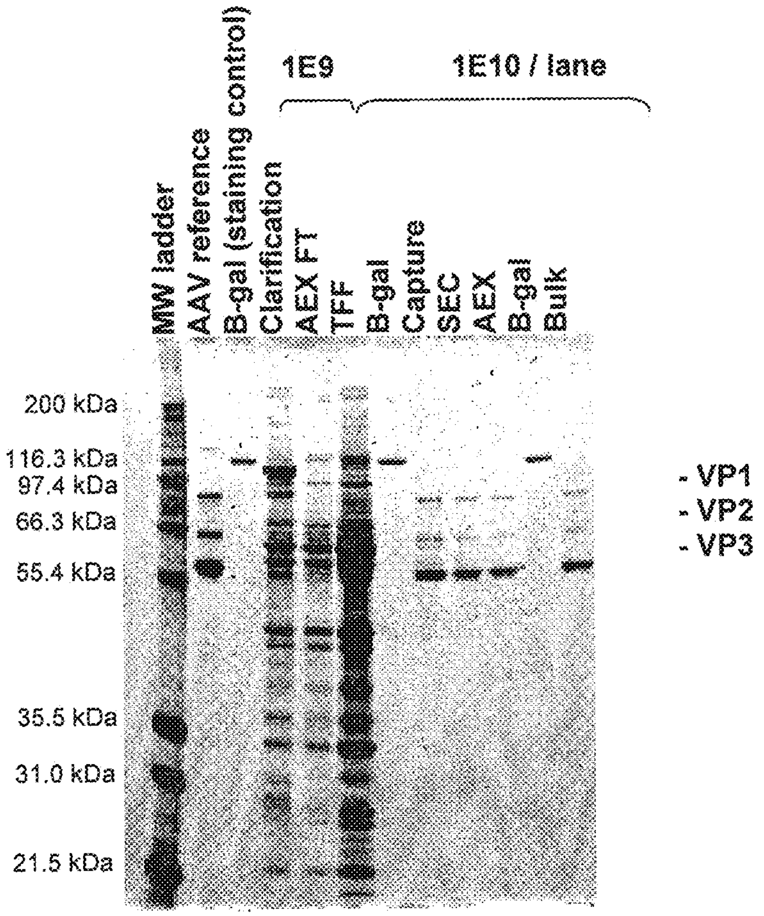
FIG. 6 shows assessment of purification across the process by SDS-PAGE. In-process samples from a representative production culture harvest were run on a denaturing/reducing 10% polyacrylamide gel and stained with Sypro orange. All post-harvest samples were loaded at $1\times10^{10}$ DRP/lane. The two upstream samples before the TFF concentration step (initial clarification step and AEX flow-through) could only be loaded at $1\times10^{9}$ DRP/lane due to volume constraints on the gel. Beta-galactosidase (B-Gal) was loaded at 50 ng/lane to assess sensitivity and consistency of staining across the gel. The three AAV1 capsid proteins (VP1, 2, and 3) are indicated.

FIG. 6 compares the degree of purification across the various process steps by SDS-PAGE. In-process samples from a representative production culture harvest were run on a denaturing/reducing 10% polyacrylamide gel and stained with Sypro Orange. All post-harvest samples were loaded at $1\times10^{10}$ DRP/lane. The two upstream samples before the TFF concentration step (initial clarification step and anion exchange ("AEX") flow-through) could only be loaded at $1\times10^{9}$ DRP/lane due to volume constraints on the gel. Beta-galactosidase (B-Gal) was loaded at 50 ng/lane to assess sensitivity and consistency of staining across the gel. The three AAV1 capsid proteins (VP1, 2, and 3) are indicated.

Example 13: Percent Recovery of rAAV During Purification

Figure 7:
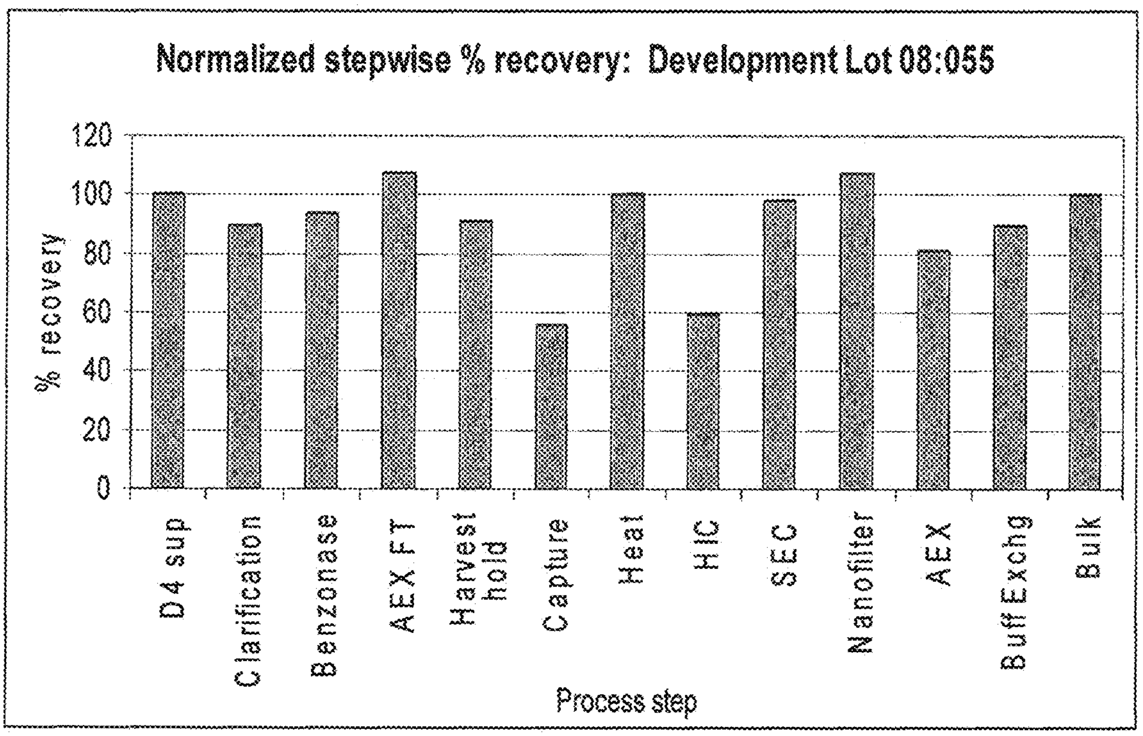
FIG. 7 shows the stepwise recovery for rAAV purification as described in Examples 1-12. The total DRP present in the supernatant prior to harvest was defined as 100%. Recovery at each step is the total DRP recovered relative to total DRP processed over that step. Overall recovery for the entire process was approximately 28%. D4 sup: production culture; AEX FT: anion exchange (Mustang® Q) flow-through; capture: apatite chromatography; heat: heat inactivation or heat kilt; HIC: hydrophobic interaction chromatography; SEC: size exclusion chromatography; AEX: anion exchange.

The data presented in FIG. 7 shows the percentage recovery of infectious rAAV particles after each process step of the purification scheme from a representative production culture of an rAAV-1 vector. The percentage recovery was calculated based on the total DRPs of the rAAV-1 vector recovered from each process step divided by the total number of DRPs loaded or subjected to that purification step. The data demonstrates that at each step in the purification process, recoveries of approximately 60% or greater were achieved. In numerous experiments, the range of recovery from each process step was at least 60% to 90%. Particularly noteworthy, the range of recovery at the capture step (i.e., the apatite chromatography step) in individual experiments ranged from 57% to greater than 90%. Furthermore, the range of recovery at the HIC step ranged from 60% to 80%.

Although the foregoing invention has been described in some detail by way of illustration and example for purposes of clarity of understanding, it is apparent to those skilled in the art that certain minor changes and modifications will be practiced. Therefore, the description and examples should not be construed as limiting the scope of the invention.

The invention claimed is:

1. A method for isolating a population of recombinant adeno-associated virus (rAAV) particles from in-process impurities in a feedstream, comprising the steps of:

(a) subjecting the feedstream containing the rAAV particles to flow-through anionic exchange filtration and/or subjecting the feedstream containing the rAAV particles to tangential flow filtration (TFF);

(b) contacting the feedstream containing the rAAV particles with an apatite chromatography medium in the presence of polyethylene glycol (PEG), wherein the rAAV particles bind to the apatite chromatography medium; and (c) eluting the rAAV particles bound to the apatite chromatography medium with an elution buffer containing less than 3% (w/v) PEG; and (d) heat inactivating a helper virus in the feedstream eluted from the apatite chromatography medium, wherein the heat inactivation step comprises heating the feedstream eluted from the apatite chromatography medium to 52° C.

2. The method of claim 1, wherein the feedstream containing the rAAV particles is subjected to flow-through anionic exchange filtration before subjecting the feedstream containing the rAAV particles to TFF.

3. The method of claim 1, wherein the apatite chromatography medium is ceramic hydroxyapatite (CHT) or ceramic fluoroapatite (CFT).

4. The method of claim 1, wherein the specific binding of the apatite chromatography medium to the rAAV particles is between $10^{14}$ and $10^{16}$ DNase-resistant particles per milliliter (DRP/mL).

5. The method of claim 1, further comprising a step of binding the rAAV particles in the feedstream eluted from the apatite chromatography medium to an anionic chromatography medium.

6. The method of claim 1, wherein the feedstream containing the rAAV particles in step (b) is contacted with an apatite chromatography medium in the presence of polyethylene glycol (PEG) and a basic buffer.

7. The method of claim 6, wherein the basic buffer is between pH 7.6 and 10.

8. The method of claim 7, wherein the basic buffer comprises borate.

9. The method of claim 1, wherein the PEG has an average molecular weight between about 5,000 (PEG5000) grams per mole and about 15,000 (PEG15000) grams per mole.

10. The method of claim 1, wherein the feedstream containing the rAAV particles in step (a) is contacted with the apatite chromatography medium in the presence of between about 3% (w/v) and about 10% (w/v) PEG.

11. The method of claim 1, further comprising a step of washing the apatite chromatography medium with a wash buffer after the feedstream is contacted with the apatite chromatography medium but before eluting the rAAV particles from the apatite chromatography medium.

12. The method of claim 11, wherein the apatite chromatography medium is washed one or more times with a wash buffer containing about 7.5% (w/v) PEG and/or a wash buffer containing about 5% (w/v) PEG.

13. The method of claim 12, wherein the apatite chromatography medium is further washed with a wash buffer containing less than about 3% (w/v) PEG and/or a wash buffer containing no PEG.

14. The method of claim 11, wherein the wash buffer comprises a buffer selected from the group consisting of borate, N-2-Hydroxyethylpiperazine-N'-2-ethanesulfonic acid (HEPES), and Tris-HCl.

15. The method of claim 11, wherein the wash buffer has a basic pH.

16. The method of claim 11, wherein the wash buffer further comprises between 100 and 500 mM of a phosphate.

17. The method of claim 11, wherein the wash buffer further comprises between 50 and 250 mM NaCl.

18. The method of claim 1, wherein the rAAV particles bound to the apatite chromatography medium are eluted with an elution buffer containing low concentrations of PEG or in the absence of PEG.

19. The method of claim 18, wherein the elution buffer comprises a buffer selected from the group consisting of borate, N-2-Hydroxyethylpiperazine-N'-2-ethanesulfonic acid (HEPES), and Tris-HCl at neutral pH.

20. The method of claim 18, wherein the elution buffer contains less than about 3% (w/v) PEG6000.

21. The method of claim 20, wherein the elution buffer further comprises less than 100 mM phosphate.

22. The method of claim 21, wherein the elution buffer further comprises 50 mM phosphate.

23. The method of claim 22, wherein the elution buffer further comprises between 50 and 250 mM NaCl.

24. The method of claim 1, wherein the rAAV particles comprise an AAV capsid protein from an AAV capsid serotype selected from the group consisting of AAV-1, AAV-2, AAV-3, AAV-4, AAV-5, AAV-6, AAV-7, AAV-8, AAV-9, AAV-10, AAV-11, AAV-12, AAV-13, AAV-14, AAV-15 and AAV-16.

* * * * *